(12) United States Patent
Ruppersberg et al.

(10) Patent No.: US 10,172,513 B2
(45) Date of Patent: Jan. 8, 2019

(54) OTOSCOPE

(71) Applicant: Helen of Troy Limited, Belleville (BB)

(72) Inventors: Peter Ruppersberg, Blonay (CH);
Albrecht Lepple-Wienhues, Pontarlier (FR)

(73) Assignee: Helen of Troy Limited, Belleville (BB)

( * ) Notice: Subject to any disclaimer, the term of this patent is extended or adjusted under 35 U.S.C. 154(b) by 367 days.

(21) Appl. No.: 14/762,430

(22) PCT Filed: Feb. 4, 2014

(86) PCT No.: PCT/EP2014/000298
§ 371 (c)(1),
(2) Date: Jul. 21, 2015

(87) PCT Pub. No.: WO2014/117959
PCT Pub. Date: Aug. 7, 2014

(65) Prior Publication Data
US 2015/0351616 A1    Dec. 10, 2015

Related U.S. Application Data

(60) Provisional application No. 61/809,048, filed on Apr. 5, 2013, provisional application No. 61/760,511, filed (Continued)

(30) Foreign Application Priority Data

| Feb. 4, 2013 | (EP) | ................................. | 13000552 |
| Feb. 4, 2013 | (EP) | ................................. | 13000553 |
| Apr. 5, 2013 | (EP) | ................................. | 13001748 |

(51) Int. Cl.
*A61B 1/227* (2006.01)
*A61B 1/07* (2006.01)
(Continued)

(52) U.S. Cl.
CPC .......... *A61B 1/227* (2013.01); *A61B 1/00009* (2013.01); *A61B 1/00057* (2013.01);
(Continued)

(58) Field of Classification Search
CPC .............................. A61B 1/227; A61B 1/2275
(Continued)

(56) References Cited

U.S. PATENT DOCUMENTS

| 4,366,811 A | 1/1983 | Riester |
| 4,380,998 A | 4/1983 | Kieffer, III et al. |

(Continued)

FOREIGN PATENT DOCUMENTS

| CN | 1829468 A | 9/2006 |
| CN | 102026574 A | 4/2011 |

(Continued)

OTHER PUBLICATIONS

Salvinelli, F., et al., "The External Ear and the Tympanic Membrane: A Three-Dimensional Study," *Scand Audiol* 20(4): 253-256, 1991.

(Continued)

*Primary Examiner* — Eric S Gibson
(74) *Attorney, Agent, or Firm* — Dinsmore & Shohl LLP

(57) ABSTRACT

An otoscope comprises a handle portion and a head portion tapering along its longitudinal axis. The head portion has a proximal end adjacent the handle portion and a smaller distal end adapted to be introduced in an ear canal of a patient's outer ear. The otoscope further comprises an electronic imaging unit positioned at the distal end of the head portion, and a probe cover moving mechanism configured to move at least a portion of an at least partially transparent probe cover adapted to be put over the head portion, especially configured to move the probe cover with respect to at least one optical axis of the electronic imaging unit. The present (Continued)

invention further refers to a probe cover for such an otoscope and to a method of identifying objects in a subject's ear.

45 Claims, 15 Drawing Sheets

Related U.S. Application Data on Feb. 4, 2013, provisional application No. 61/760,507, filed on Feb. 4, 2013.

(51) Int. Cl.

| | |
|---|---|
| A61B 1/00 | (2006.01) |
| A61B 1/06 | (2006.01) |
| A61B 5/01 | (2006.01) |
| A61B 5/00 | (2006.01) |
| A61B 5/11 | (2006.01) |
| A61B 1/05 | (2006.01) |
| A61B 5/107 | (2006.01) |
| A61B 5/06 | (2006.01) |

(52) U.S. Cl.
CPC ...... *A61B 1/00066* (2013.01); *A61B 1/00101* (2013.01); *A61B 1/00142* (2013.01); *A61B 1/00179* (2013.01); *A61B 1/00193* (2013.01); *A61B 1/05* (2013.01); *A61B 1/051* (2013.01); *A61B 1/0623* (2013.01); *A61B 1/0638* (2013.01); *A61B 1/07* (2013.01); *A61B 1/2275* (2013.01); *A61B 5/0075* (2013.01); *A61B 5/01* (2013.01); *A61B 5/1077* (2013.01); *A61B 5/11* (2013.01); *A61B 5/6817* (2013.01); *A61B 5/7203* (2013.01); *A61B 5/7221* (2013.01); *A61B 5/7246* (2013.01); *A61B 5/7264* (2013.01); *A61B 5/7275* (2013.01); *A61B 5/74* (2013.01); *A61B 5/065* (2013.01); *A61B 5/6885* (2013.01); *A61B 5/6886* (2013.01); *A61B 2562/0242* (2013.01)

(58) Field of Classification Search
USPC .......................................................... 600/200
See application file for complete search history.

(56) References Cited

U.S. PATENT DOCUMENTS

| | | | |
|---|---|---|---|
| 4,685,452 A | 8/1987 | Riester | |
| 4,766,886 A | 8/1988 | Juhn | |
| 5,280,378 A | 1/1994 | Lombardo | |
| 5,319,199 A | 6/1994 | Stedman et al. | |
| 5,363,839 A | 11/1994 | Lankford | |
| 5,445,157 A | 8/1995 | Adachi et al. | |
| 5,868,682 A | 2/1999 | Combs et al. | |
| 5,919,130 A | 7/1999 | Monroe et al. | |
| 5,935,058 A | 8/1999 | Makita et al. | |
| 5,951,486 A | 9/1999 | Jenkins et al. | |
| 6,165,035 A | 12/2000 | Avner | |
| 6,898,457 B1 | 5/2005 | Kraus et al. | |
| 7,529,577 B2 | 5/2009 | Jensen et al. | |
| 2002/0087084 A1 | 7/2002 | Shahar et al. | |
| 2003/0108083 A1 | 6/2003 | Seitz | |
| 2003/0139672 A1 | 7/2003 | Cane et al. | |
| 2004/0136010 A1 | 7/2004 | Jensen et al. | |
| 2005/0027168 A1 | 2/2005 | Strom et al. | |
| 2005/0192482 A1 | 9/2005 | Carpenter et al. | |
| 2005/0228231 A1 | 10/2005 | MacKinnon et al. | |
| 2006/0282009 A1 | 12/2006 | Oberg et al. | |
| 2007/0112273 A1 | 5/2007 | Rogers | |
| 2008/0249369 A1 | 10/2008 | Seibel et al. | |
| 2009/0030295 A1 | 1/2009 | Shioi et al. | |
| 2009/0182526 A1 | 7/2009 | Quinn et al. | |
| 2009/0318758 A1 | 12/2009 | Farr et al. | |
| 2010/0060718 A1 | 3/2010 | Forster et al. | |
| 2011/0063428 A1 | 3/2011 | Sonnenschein et al. | |
| 2011/0112791 A1 | 5/2011 | Pak et al. | |
| 2011/0137118 A1 | 6/2011 | Huang | |
| 2011/0257481 A1 | 10/2011 | Ogawa et al. | |
| 2012/0059224 A1 | 3/2012 | Wellen et al. | |
| 2012/0130168 A1 | 5/2012 | Konomura | |
| 2012/0179187 A1 | 7/2012 | Loushin et al. | |
| 2012/0253166 A1 | 10/2012 | Ahn et al. | |
| 2012/0327426 A1 | 12/2012 | Hart et al. | |
| 2013/0027515 A1 | 1/2013 | Vinther et al. | |
| 2013/0083823 A1 | 4/2013 | Harr et al. | |
| 2013/0237754 A1 | 9/2013 | Berglund et al. | |
| 2013/0296685 A1 | 11/2013 | Tsuboi et al. | |
| 2015/0351606 A1 | 12/2015 | Ruppersberg et al. | |
| 2015/0351607 A1 | 12/2015 | Ruppersberg et al. | |
| 2015/0351620 A1 | 12/2015 | Ruppersberg et al. | |
| 2015/0351637 A1 | 12/2015 | Ruppersberg et al. | |
| 2015/0374208 A1 | 12/2015 | Ruppersberg et al. | |

FOREIGN PATENT DOCUMENTS

| | | |
|---|---|---|
| EP | 0 472 490 B1 | 2/1992 |
| EP | 1 134 565 A1 | 9/2001 |
| EP | 1 477 107 A1 | 11/2004 |
| EP | 2 014 220 A1 | 1/2009 |
| EP | 2 289 391 A1 | 3/2011 |
| EP | 2 2774 439 A2 | 1/2012 |
| JP | 63-40117 A | 2/1988 |
| JP | 5-253184 A | 10/1993 |
| JP | 7-111987 A | 5/1995 |
| JP | 9-19403 A | 1/1997 |
| JP | 11-28194 A | 2/1999 |
| JP | 11-113841 A | 4/1999 |
| JP | 11-316157 A | 11/1999 |
| JP | 2000-30063 A | 1/2000 |
| JP | 2001-517105 A | 10/2001 |
| JP | 2002-135887 A | 5/2002 |
| JP | 2002-528158 A | 9/2002 |
| JP | 2004-535834 A | 12/2004 |
| JP | 2005-519666 A | 7/2005 |
| JP | 2007-130084 A | 5/2007 |
| JP | 2007-144103 A | 6/2007 |
| JP | 2007-236734 A | 9/2007 |
| JP | 2009-153664 A | 7/2009 |
| JP | 2009-178482 A | 8/2009 |
| JP | 2009-201853 A | 9/2009 |
| JP | 2011-62370 A | 3/2011 |
| JP | 2011-72638 A | 4/2011 |
| JP | 2011-104333 A | 6/2011 |
| JP | 2011-520501 A | 7/2011 |
| JP | 2012-514200 A | 6/2012 |
| JP | 3178405 U | 8/2012 |
| JP | 2013-202260 A | 10/2013 |
| JP | 2014-525774 A | 10/2014 |
| JP | 2015-530886 A | 10/2015 |
| KR | 10-2006-0122567 A | 11/2006 |
| TW | 201225896 A | 7/2012 |
| WO | 02/39874 A2 | 5/2002 |
| WO | 2007/049562 A1 | 5/2007 |
| WO | 2009/139548 A2 | 11/2009 |
| WO | 2009/157825 A1 | 12/2009 |
| WO | 2012/061697 A1 | 5/2012 |
| WO | 2013/002935 A1 | 1/2013 |
| WO | 2013/016651 A1 | 1/2013 |

OTHER PUBLICATIONS

Wäny, M., et al., "Utrasmall Digital Image Sensor for Endoscopic Applications," in *Proc. of 2009 International Image Sensor Workshop*, Bergen, Norway, Jun. 22-28, 2009, 4 pages.

Wilke, M., et al., "Prospects and Limits in Wafer-Level-Packaging of Image Sensors," Electronic Components and Technology Conference (ECTC), 2011 IEEE 61st, Lake Buena Vista, Florida, May 31-Jun. 3, 2011, pp. 1901-1907.

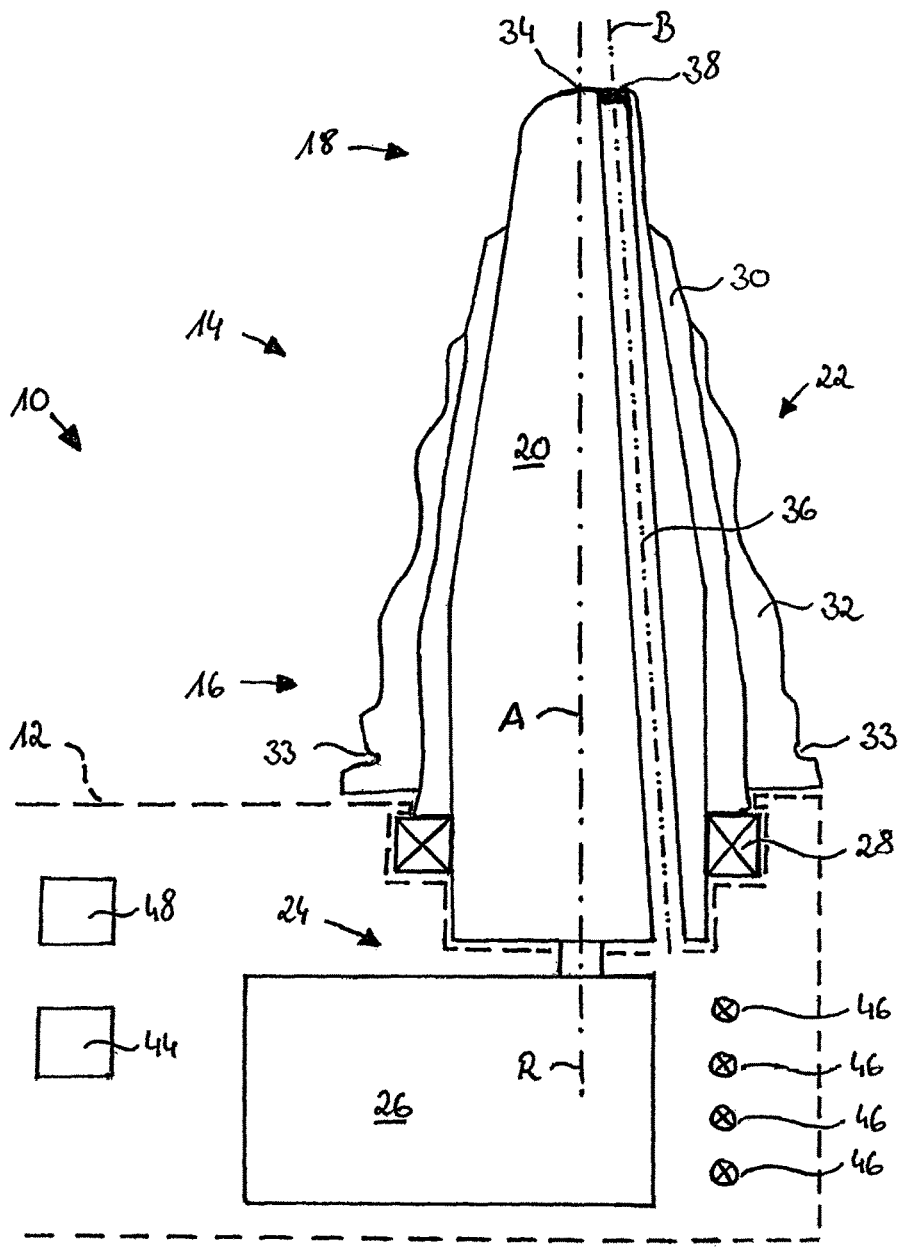
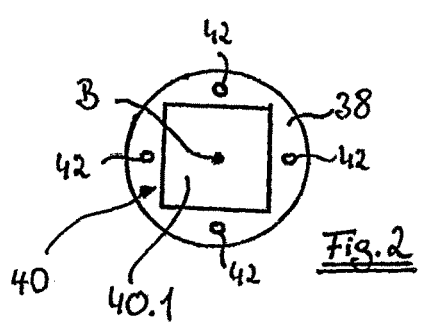
Fig. 1
Fig. 2

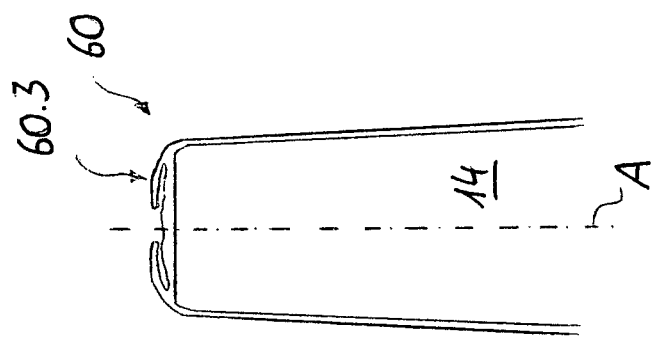
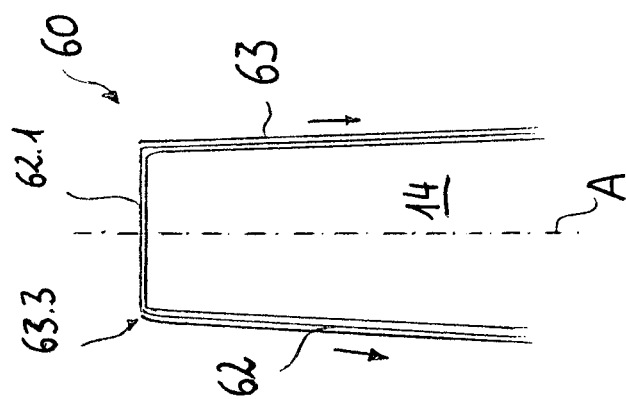
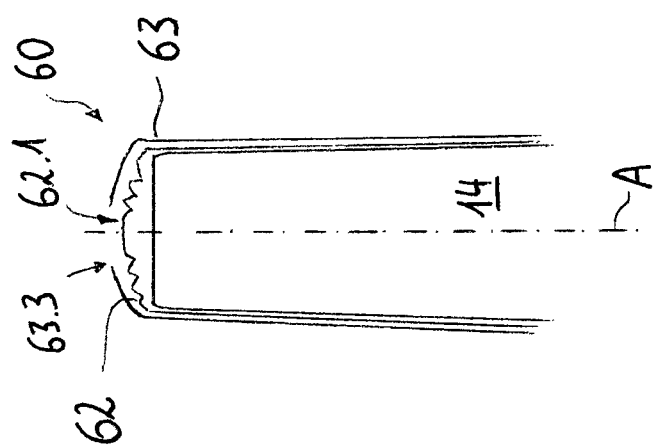

OTOSCOPE

FIELD OF THE INVENTION

The invention refers to an otoscope comprising a handle portion allowing a user to manipulate the otoscope during its application, and further comprising a head portion exhibiting a substantially tapering form extending along a longitudinal axis of the head portion, wherein the head portion has a proximal end adjacent to the handle portion and a smaller distal end adapted to be introduced in an ear canal of a patient's outer ear. Further, the invention refers to a probe cover for such an otoscope and to a method of identifying objects in a subject's ear.

An otoscope (sometimes also called "auriscope") is a medical device which is used to look into ears. The corresponding method of doing so is called "otoscopy". Otoscopy is a standard medical examination technique established more than 100 years ago. Medical students learn otoscopy early in their studies during the practical course in physiology. Typical diagnoses based on otoscopic examination are: otitis media (OM), otitis media with effusion (OME), otitis externa, and eardrum perforation. OME is defined by the presence of middle ear effusion, i.e. a liquid behind an intact tympanic membrane without signs or symptoms of acute infection. OME is one of the most frequent pediatric diagnoses. However, otoscopy is also used to generally identify and observe object's in the ear, such as earwax, hair and the eardrum.

A typical otoscope 10' as used for decades in otoscopy is shown in FIG. 3. The otoscope 10' comprises a handle portion 12' allowing the user to manipulate the otoscope during its application. The term "to manipulate" in this context refers to different kinds of manipulation, such as—but not limited to—holding the otoscope, aligning the otoscope with respect to the patient's ear, and turning on or off a light. The otoscope 10' further comprises a head portion 14' connected to the handle portion 12'. The head portion 14' exhibits a substantially tapering form—usually a conical form—extending along a longitudinal axis A' of the head portion 14'. The head portion 14' is substantially comprised of an empty funnel, wherein the tip of the funnel typically has a relatively small diameter of 3 millimeters, e.g. about 3 millimeters for children. Furthermore, the head portion 14' has a proximal end 16' adjacent to the handle portion 12' and a smaller distal end 18' adapted to be introduced in an ear canal C of a patient's outer ear. The term "end" in this context does not mean a single point but rather refers to a region or section of the head portion 14', wherein the proximal end 16' is located opposite to the distal end 18' with respect to the longitudinal axis A'. The ear canal C is partly surrounded by soft connective tissue C1 and—further down towards the middle ear—partly by hard bone C2.

The working principle of the known otoscope is typically to observe and simultaneously illuminate the patient's eardrum ED through the empty funnel with the 3 mm tip pushed deeply into the ear canal C. Normally, the eardrum ED is not visible from outside the ear, due to the natural curvature of the ear canal C. In order to overcome the natural curvature of the ear canal C, the skilled physician has to carefully pull the outer ear upward and to the back while carefully pushing the tip of the funnel as deeply as necessary to observe the eardrum. The ear canal C has to be deformed (especially straightened) in such a way that the physician has a free view onto the eardrum ED along the optical axis of the otoscope 10', wherein the optical axis corresponds to the longitudinal axis A' of the head portion 14'. The optics of an otoscope is situated only at the wider end of the funnel at its proximal end 16' and essentially consists of a lamp and a lens (not shown) to magnify the image of the eardrum ED.

The otoscopy procedure needs manual skills and significant training to make it possible to carefully push the funnel into the ear canal C while looking inside and manipulating the curvature of the ear canal C by pulling the ear. For example, it is very important for the trained physician to brace the hand holding the otoscope against the patient's head to avoid injury to the ear canal C by placing the index finger or little finger against the head. In particular in young children—where the inner part of the ear canal is relatively short and sudden head movement during the examination may occur—there is a risk of penetration of the very sensitive ear canal skin or even of the eardrum ED. Besides pain and handicapped hearing, such an injury may even induce cardiovascular complications through a vagal overstimulation and therefore has to be avoided by all means.

Furthermore, especially in an inflamed ear, the mechanical manipulation of "straightening" the ear canal C typically causes considerable discomfort or even pain, rendering the examination of an infant even more difficult.

FIG. 4 illustrates that with a distal tip of the otoscope 10' being positioned far within the bony part C2, the ear canal C has to be "straightened" considerably in such a way that the longitudinal axis A is directed onto the eardrum ED, at least approximately. The distal tip of the head portion 14' is supported within the bony part C2, such that a proximal end of the head portion 14' contacting the soft connective tissue C1 can push the soft connective tissue C1 downwards. The head portion 14' is shaped such that there remains the danger of touching the eardrum ED.

BACKGROUND OF THE INVENTION

For the above reasons, reliably and securely handling an otoscope of the art is currently subject to only well trained physicians and not amenable to the larger community of practitioners. A study recently published in the US as a result of a survey has shown that even physicians often fail to (correctly) determine the status of e.g. the subject's eardrum or fail to correctly interpret the image provided by the otoscope (i.e. correct and meaningful object recognition). Such failures result in misinterpretation of the status of the inner ear canal or the eardrum. As a consequence, e.g. over-medication with antibiotics for treating supposed inflammations of the eardrum occurs, because physicians tend to err on the side of caution, or meaningless image interpretation occurs.

Notably, there also exist other otoscopic devices, as e.g. video otoscopes, allowing a skilled expert to capture images of the subject's eardrum and the ear canal. Such video otoscopes comprise a bundle of light guides extending from the distal end of the head portion to a CCD-chip located remote from the distal end. The achievable resolution of the images depends on the number of light guides. In order to obtain images having a satisfying resolution, a significant number of individual light guides must be provided rendering devices by far too expensive for routine care. Moreover, all of the known video otoscopes having the CCD-chip located remote from the distal end of the head portion require superior handling skills by the physician. For the above reasons, they are not configured and suitable for domestic use by a larger community of practitioners, nor use by laypersons.

All otoscopes currently on the market—including video otoscopes—generally are based on the following fundamental design: a relatively thin open funnel. Length, angle, field of vision and size of the funnels are essentially similar for all marketed otoscopes. As a result of these common characteristics, ease of use (due to safety issues) is limited for such devices. Methods for reliable detection of objects in the ear canal, including the eardrum, are remarkably intricate with such known otoscopes.

Consequently, until today otoscopy has almost been exclusively applied by medical doctors. And even among medical doctors, only a minor percentage is sufficiently trained to carry out otoscopy in a reliable and appropriate way. However, since otitis media is the most frequent disease causing high fever in young children, and to exclude otitis media, especially OME, is a major reason for seeing a pediatrician, there is an urgent need for a parental check of the ear. Parents may also benefit from an otoscope that can be securely used by laypersons at home in order to check whether an ear canal of their child is blocked by massive earwax and/or foreign objects.

Prior art document U.S. Pat. No. 5,910,130 A describes an otoscope with a miniature video camera or a solid-state imager, e.g. a CCD or CMOS. A light source can be provided in the form of a continuous ring of light emitting fibres. The head portion of the otoscope has to be introduced far into a straightened ear canal in order to observe the eardrum.

Prior art document EP 2 289 391 A1 describes an otoscope with a head portion and a fastening ring for reversibly mounting the head portion to a display portion.

It is therefore an object of the present invention to provide an otoscope that allows for domestic application by laypersons and medical doctors without extensive otoscopy training and without any—or at least with a significantly reduced—risk of causing injuries to the patient. In particular, it is an object of the present invention to provide an otoscope that allows for domestic application by laypersons without the need of cleaning, especially sterilizing, the otoscope, i.e. with minimized danger of infections, especially without restricting the ability of identifying objects within the ear canal. The object of the present invention can also be describes as to provide a method allowing for reliably identifying objects within the ear canal, any danger of infections being minimized.

This object is achieved according to the present invention by an otoscope exhibiting the features of claim 1 or by a probe cover exhibiting the features of the respective independent claim or by a method of identifying objects in a subject's ear, the method exhibiting the features of the respective independent claim. Preferred embodiments represent the subject-matter of the respective dependent claims.

In particular, this object is achieved by an otoscope of the generic type as described above, wherein the otoscope further comprises an electronic imaging unit positioned at the distal end of the head portion, especially at a distal tip of the head portion, wherein the otoscope further comprises a probe cover moving mechanism configured to move at least a portion of an at least partially transparent probe cover adapted to be put over the head portion, especially configured to move the probe cover with respect to at least one optical axis of the electronic imaging unit.

With an otoscope comprising a probe cover moving mechanism, artifacts, such as earwax particles, adhering to the probe cover and obstructing the view of the electronic imaging unit or camera onto the eardrum can be moved away by the probe cover moving mechanism. In particular for hygienic reasons, in most of the use cases, the otoscope is coupled with an at least partially transparent probe cover adapted to be put over the head portion. The probe cover may be made from a plastic material, preferably from a transparent plastic material. Such a probe cover may be designed as a single-use product that can be produced in larger numbers with low costs. The probe cover shall be transparent, at least at the locations where it covers an observation point, especially an eccentric observation point, i.e. where it intersects an optical axis of the electronic imaging unit, so as to allow the electronic imaging unit to have a clear view onto the eardrum. The probe cover also inhibits contamination of the head portion of the otoscope comprising the electronic imaging unit, in particular when introducing the head portion into the patient's ear canal.

The probe cover moving mechanism can be provided e.g. in the form of a latch mechanism or an automatized mechanism which is driven by a motor. The probe cover moving mechanism allows for controlled, predefined relative displacement, especially in an axial direction, i.e. parallel to the longitudinal axis of the head portion. Preferably, the probe cover moving mechanism is configured for interacting with a proximal portion of the probe cover and is configured for an axial motion or displacement of the probe cover or a portion of the probe cover, be it in a distal and/or in a proximal direction. As an alternative or in addition, the probe cover moving mechanism can be configured for rotating the probe cover.

According to one embodiment, the moving mechanism is configured to move the probe cover in a direction which is at least approximately parallel to the longitudinal axis, especially by exerting a pulling force on the probe cover. Such a moving mechanism may ensure homogeneous tension within the probe cover and may homogeneously press the probe cover onto the outer surface of the head portion, especially in conjunction with a conical shape of the head portion. Also, such a moving mechanism can conveniently interfere with the probe cover at a proximal end of the probe cover.

Preferably, in addition, the moving mechanism is configured to move at least a portion of a reservoir of the probe cover in a direction which is at least approximately orthogonal to the longitudinal axis. Such a moving mechanism may ensure that ear wax or any other particles obstructing the view can be displaced out of the line of sight effectively, especially in conjunction with radially offset optical axes.

According to one embodiment, the moving mechanism is configured to unfold a/the reservoir of the probe cover by stretching a distal portion of the probe cover. Such a moving mechanism may ensure that ear wax or any other particles obstructing the view can be displaced away from the distal tip of the head portion effectively.

According to one embodiment, the electronic imaging unit exhibits at least one optical axis which is positioned radially offset from the longitudinal axis, the moving mechanism being configured to move the probe cover with respect to the at least one radially offset optical axis. Providing a small electronic imaging unit (or an electronic imaging unit with optical components having small radial dimensions) at the distal end of the head portion exhibiting at least one optical axis which is radially offset allows to "see" the patient's eardrum without the need to deform the patient's ear canal, or at least without having to deform the ear canal to such an extent as with the above described conventional otoscope. The reason for this is that there is no need for the "viewing direction" of the electronic imaging unit to correspond to the longitudinal axis of the head portion of the otoscope. Rather, the radial offset can ensure that there is a line of sight onto the eardrum even if the ear canal is not straightened, allowing the device to "look around the corner".

In particular, in many cases, the ear canal of the outer ear is not straight-lined, but exhibits at least one curvature, especially at a transition area or transition point between soft connective tissue and hard bone confining the ear canal. The "corner" is provided by this curvature. In particular, virtually almost always, the ear canal has an S-shaped (sigmoid) form with a first curvature and a second curvature, the second curvature being closer to the eardrum than the first curvature. Particularly, the second curvature of the ear canal obstructs any optical line of sight or visual communication of an otoscope which is not introduced as far as at least some millimeters within the bony part of the ear canal. The "corner" can be defined as the second curvature of the ear canal. In particular, in a distal direction, the second curvature leads to the bony part of the ear canal. A transition point or area between soft connective tissue and hard bone is arranged at this second curvature, at least most often. The second curvature leads into the section of the ear canal which is exclusively confined by hard bone. Preferably, the transition area can be defined as an area of about a few millimeters distal to (behind) and about a few millimeters proximal to (in front of) a curvature, especially 0 mm to 5 mm or 1 mm to 3 mm.

In particular, the probe cover moving mechanism may ensure that an optical axis of the electronic imaging unit can be arranged with a relatively large radial offset, especially without evoking the problem of any earwax particles obstructing visibility or with reduced probability of such earwax particles. Earwax particles are often arranged at an inner surface surrounding the ear canal. Thus, for an optical axis being arranged with a high radial offset, i.e. close to an inner lateral surface of the ear canal, there may be an increased likelihood of earwax particles adhering to the probe cover at a section covering the optical axis, thereby obstructing the view onto the eardrum. In other words: There may be an increased likelihood of earwax particles obstructing the view from an optical axis which is radially offset than from an optical axis which is arranged at least approximately centrically. The probe cover moving mechanism can ensure that the view onto the eardrum is not obstructed, even in case the optical axis is arranged with a maximum radial offset close to an inner lateral surface of the ear canal. Thus, the present invention is based on the finding that by providing a probe cover moving mechanism, observation of the eardrum from an eccentric observation point with a relatively large radial offset can be made more practicable and more reliable. A probe cover moving mechanism can ensure that the concept of "looking around the corner" is feasible and can be realized in a convenient way, even in case the ear canal is obstructed by several objects.

In particular, for displacing any particles or ear wax out of the line of sight, a relative motion or displacement of the probe cover induced by the moving mechanism is most effective in case the optical axis is positioned radially offset, especially with a maximum radial offset. The present invention is based on the finding that in most cases, it may be most favorable displacing the entire probe cover, apart from a central distal point at the distal tip of the probe cover. In other words: The whole probe cover can e.g. be pulled backwards in a proximal direction, except for a central distal point at the distal tip of the probe cover. At this distal point, preferably, a probe cover reservoir is provided. Thus, relative motion between the probe cover and the head portion may be minimum at the distal point, but maximum at any point of the distal tip which is positioned radially offset.

An otoscope exhibiting a probe cover moving mechanism in conjunction with a radially offset electronic imaging unit may be used by laypersons, without extensive otoscopy training and with a significantly reduced risk of causing injuries, especially with a significantly reduced risk of irritation of the patient's tissue, e.g. the tissue within the hard bone section of the ear canal. Such an otoscope allows for observing the eardrum substantially irrespective of the relative position of a head portion within the ear canal, especially irrespective of any specific insertion depth into the bony part of the ear canal, i.e. the section confined by hard bone. As the otoscope is arranged for "looking around the corner or curvature", the layperson does not have to introduce the head portion as far as a section of the ear canal which is confined by hard bone.

While in traditional otoscopy, the physician has to introduce the otoscope at least as far as some millimeters within the bony part of the ear canal, i.e. considerably further inwards than the second curvature, an otoscope according to the present invention can be positioned adjacent to the second curvature. In traditional otoscopy, the otoscope is necessarily introduced far into the bony part of the ear canal, especially in order to provide a kind of support or rest or anchoring point at the distal tip of the otoscope. Once the distal tip of the otoscope is supported within the bony part, the physician can apply a leverage on the handle portion of the otoscope, in order to straighten the ear canal and in order to ensure an optical line of sight onto the eardrum. But, this kind of "alignment" of the otoscope or this kind of straightening out the ear canal is painful. In contrast, the otoscope according to the invention does not require such an "alignment" or straightening.

Preferably, the radial offset is at least factor 0.25 of the radial dimension of the distal end, preferably at least factor 0.3, more preferable at least factor 0.35. Such a relatively large radial offset can ensure positioning the optical axis in a favorable eccentric observation point within the ear canal, even in case the distal tip in introduced only as deep as a transition point between soft connective tissue and hard bone. According to one embodiment, the at least one optical axis is arranged as close as possible to an inner lateral surface of the distal end. Thereby, the radial offset can be maximized.

Preferably, the electronic imaging unit or at least an optical component thereof, e.g. a lens, is positioned at the most distal part of the head portion. In particular, the electronic imaging unit can be in contact with a front side or front face of the head portion, or the electronic imaging unit can provide a front side or front face of the head portion. This enables positioning the electronic imaging unit most distal within the ear canal without the need of introducing the head portion deep into the ear canal.

The otoscope according to the present invention may comprise further features that are provided, for example, by modern digital photo cameras. For example, the otoscope may comprise visual output means, such as a display, and/or acoustic output means, such as a loudspeaker, and/or a storage card slot for inserting a storage card to store the acquired images, and/or a cable connection port, such as an USB-port, and/or a wireless connection, such as Bluetooth®, WIFI®, and/or an energy supply, such as a battery.

Preferably, an "optical axis of the electronic imaging unit" is an axis which extends from a most distal point of the electronic imaging unit in a distal direction, especially towards the eardrum, wherein its orientation is not modified any more by any optical components. The "optical axis of the electronic imaging unit" of an electronic imaging unit preferably is the optical axis with the largest radial offset.

The electronic imaging unit may comprise a video camera defining an optical axis, preferable a wide angle color video camera. The term "wide angle" in this context refers to angels of at least 80°, preferably of at least 110°, e.g. 120°. Such wide angle cameras allow detection of the patient's eardrum, even if the optical axis of the camera is not directly centered to the eardrum and even if the eardrum is relatively remote from the camera, compared to the distance between the eardrum and the tip end of a conventional otoscope head during application. Using a color video camera is advantageous, allowing determination of the color of the eardrum and/or of the inner portion of the ear canal. Thus, inflammations can be detected by the degree of reddishness.

The electronic imaging unit may comprise a miniature camera, in particular a wafer-level camera of a substantially flat configuration, having dimensions of less than 3 mm×3 mm, preferably less than 2 mm×2 mm, especially 1.2 mm×1.2 mm, even more preferable of about 1 mm×1 mm or even less than 1 mm×1 mm. Wafer-level cameras refer to a relatively new technology. They can be produced small in size with only about 3 microns per pixel. Therefore, wafer-level imaging technology allows obtaining images of "sufficient" resolution of the eardrum, e.g. images of 250 pixels× 250 pixels, with a footprint of the camera including lens of only about 1 mm×1 mm or even smaller.

The term "miniature camera" refers to cameras having minimum dimensions with respect to the required method of capturing images, preferably lateral or radial dimensions in the range of 0.5 mm to 2.5 mm, more preferably in the range of 0.5 mm to 1.5 mm, or 1 mm. A "miniature camera" may exhibit a diameter in the range of e.g. 0.5 mm to 1.5 mm. The dimensions of the camera in an axial direction (parallel to the longitudinal axis) is circumstantial, i.e. only of minor importance. Radial dimensions of less than 2 mm×2 mm, even more preferable of about 1 mm×1 mm provide the advantage that an optical axis of the electronic imaging unit or camera can be arranged very close to an inner or outer lateral surface of the head portion, thereby enabling the otoscope to "look around the corner" with a relatively big angle, e.g. an angle in the range of 10° to 60°, preferably in the range of 15° to 40°, more preferable in the range of 20° to 30°.

A camera based on wafer technology provides a good compromise between light sensitivity and space requirements. The light sensitivity depends on the dimensions of an aperture or lens of the camera. The bigger the aperture, the higher the light sensitivity.

One optical axis of the electronic imaging unit may be positioned substantially centrically with respect to the longitudinal axis of the head portion. If one optical axis of the electronic imaging unit is positioned on the longitudinal axis of the head portion, a substantially flat optical component of the electronic imaging unit is preferable inclined or inclinable with respect of the longitudinal axis of the head portion, so that the one optical axis (or a "viewing direction") of the electronic imaging unit is angled with respect to the longitudinal axis (tilted against the longitudinal axis) of the head portion, allowing the otoscope to "look around the corner" even from a central observation point.

The electronic imaging unit may comprise at least one optical axis, e.g. provided by a camera, preferably at least three or four optical axes provided by at least three or four wafer-level cameras which is/are positioned radially offset from the longitudinal axis of the head portion. Such a configuration also allows obtaining a free view onto the eardrum without having to introduce the electronic imaging unit as deeply as it would be necessary if the electronic imaging unit only had one optical axis placed just centrally on the longitudinal axis of the head portion. The offset may be at least 1 mm, preferably at least 2 mm, more preferably at least 2.5 mm from the longitudinal axis. Preferably, the maximum radial offset is within the limits of the outer diameter of a distal tip of the head portion.

The head portion is preferably shaped such and exhibits radial dimensions such that its distal end comprising the electronic imaging unit can be introduced only as deep into the ear canal as not to touch the eardrum, especially only as deep as not to touch the hard bone, or at most only as far as some millimeters within the section confined by hard bone. The ear canal of the patient's outer ear is limited by the eardrum. Notably, the ear canal of the patient's outer ear comprises an outer part which refers to a portion of the patient's outer ear (i.e. the patient's external auditory canal) that is surrounded by soft connective tissue and that usually comprises hair and earwax. The outer part comprises approximately the outer half of the ear canal of the patient's outer ear. Furthermore, the ear canal of the patient's outer ear also comprises an inner part which refers to a portion of the patient's outer ear (i.e. the patient's external auditory canal) that is surrounded by hard skull bone and that is usually free from any hair and earwax. This portion extends from the proximal end the outer part of the ear canal of the patient's outer ear to the eardrum. The inner part of the ear canal is very sensitive to pain in case of injury by mechanical friction. Injuring the inner part of the ear canal even bears the risk of cardiovascular complications through vagal overstimulation.

Preferably, the head portion is shaped in such a way that its distal end comprising the electronic imaging unit can be introduced only in an area of the ear canal which is confined by soft connective tissue, but not in an area of the ear canal which is confined by hard bone. On the one hand, such a shape can ensure that the distal end does not touch the eardrum, even if the otoscope is applied by laypersons. On the other hand, the otoscope can be applied by layperson without the need of correcting the position of the head portion within the ear canal. Rather, the head portion only has to be positioned "somehow" within the ear canal, which even can be made by the same person. In other words: There is no need of any assistance at all, which is favorable e.g. for an application by older people living on one's own. The otoscope according to the present invention even can enable an application by the layperson. In particular, the otoscope is arranged to "look around the corner" such that it is sufficient to introduce the head portion only in an area of the ear canal which is confined by soft connective tissue.

Introducing the head portion only in an area of the ear canal which is confined by soft connective tissue can ensure that there is reduced friction between an inner lateral surface of the ear canal and the probe cover during displacement of the probe cover. Introducing the head portion not as deep as in an area of the ear canal which is confined by hard bone can ensure that any relative motion between the probe cover and the inner lateral surface of the ear canal does not irritate any tissue which is pain sensitive.

Preferably, a tip portion of the distal end can be introduced into the ear canal of the patient's outer ear no further than to a distance from the eardrum of at least a few millimeters, preferably of at least 3 mm, more preferable of at least 10 mm, further preferred of at least 15 mm.

As already mentioned above, the tapering head portion of the otoscope according to the present invention can be shaped with a blunt, rounded tip end, as compared to a conventionally known otoscope, thereby reducing the risk of introducing injury or discomfort to the patient. Thus, the device can be securely handled by laypersons. The otoscope according to the present invention, nevertheless, allows detecting the eardrum, since the electronic imaging unit is provided at the distal end of the head portion, and any objects adhering the probe cover and obstructing vision into the ear canal, especially onto the eardrum, can be displaced by displacing the probe cover.

Preferably, the distal end of the head portion is provided with a round and smooth shape. Moreover, the distal end may be made from a relatively soft material, such as silicone, or it may comprise an outer surface made of such a soft material. Furthermore, the longitudinal force upon introduction into the ear canal can be limited by a telescoping mechanism or the use of an elastic element.

The functional concept of a conventional otoscope as described above, however, requires the tip end of the head portion to be relatively small and acute (sharp), usually having a diameter of only about 3 mm. It is noted that the diameter of the inner part of the outer ear canal of an adult is about 4 mm. Therefore, if the user (untrained) does not pay attention, the tip portion might be introduced deeply into the inner part of the outer ear canal causing serious injuries to the patient. To substantially avoid this risk, the head portion of the otoscope according to the present invention (also having a tapered shape) preferably exhibits a diameter of at least 4 mm, preferably of more than 5 mm, more preferably of more than 6 mm, at a position along the longitudinal axis of the head portion of no more than 4 mm from a distal end point of the head portion. Thus, it is geometrically excluded to introduce the distal end of the head portion too far into the subject's ear canal. Different geometries of tapers may preferably be used according to the age group of the subject. For children, for example, the head portion of the otoscope adapted to carry out the method according to the present invention may exhibit a diameter of about 5 mm at a position along the longitudinal axis of the head portion of no more than 4 mm away from a distal end point of the head portion. For example, the head portion can be provided with a first specific shape for children at the age of 0 to 2 years and with a second specific shape for any patient at the age of more than 2 years. But, it is not necessarily required to use different geometries of tapers according to the age group of the subject. Rather, the inventive shape of the head portion can be used by all age groups, as it is not required to introduce the head portion far into the subject's ear canal. Thus, the inventive shape of the head portion can provide a universal speculum.

Preferably, the distal tip of the head portion exhibits an diameter, especially an outer diameter, of at least 4.0 mm, at least 4.7 mm, preferably of more than 4.8 mm, more preferably about 4.9 mm. A head portion with a distal tip having a diameter, especially an outer diameter, of about 4.7 mm, 4.8 mm or 4.9 mm is not adequate or appropriate for classical otoscopy, especially for observing the eardrum of a child. Such a relatively large tip could not be inserted into the ear canal as far as considerably within the bony part, especially in childrens' ears. The head portion would be blocked at a position too far away from the eardrum, at least within ears of children. It would not be possible to observe the eardrum. There would not be any line of sight onto the eardrum. It would not be possible to align the otoscope within the ear canal such that the eardrum is visible. The head portion would not be introduced far enough for aligning the entire ear canal.

In contrast, according to the present invention, a distal tip with a diameter of about 4.7 mm, 4.8 mm or 4.9 mm can ensure that the distal tip cannot be inserted further into the ear canal than a position within the part of the ear canal which corresponds to a transition area between soft connective tissue and hard bone surrounding the ear canal. In particular, at most, the distal tip of the head portion is docked to or coupled to a proximal end of the bony part. At most, the distal tip of the head portion is positioned at the outer end of the bony part of the ear canal, but not further inwards. In other words: The head portion of the otoscope is preferably shaped in such a way that its distal end comprising the electronic imaging unit or optical component (e.g. camera) can be introduced only as deep into the ear canal as a transition area between soft connective tissue and hard bone confining the ear canal. Preferably, a diameter of an inner lateral surface of the distal end is in the range between at least 4.2 mm, preferably more than 4.4 mm, more preferably about at least 4.5 mm or 4.6 mm, in order to allow maximum radial offset.

The head portion may exhibit a conical portion with an opening angle $\alpha$ in the range of 3° to 10°, preferably 4° to 8°, especially 5° or 6°. Such opening angles can ensure that, in case the layperson tries to introduce the head portion as far as a section of the ear canal which is confined by hard bone, further insertion of the head portion is blocked within the ear canal well before reaching the eardrum.

Preferably, the head portion exhibits a distal tip with a first diameter ($d_1$) in the range of 4 mm to 6 mm, preferably 4.5 mm to 5.3 mm, further preferred 4.7 mm to 5.1 mm, especially 4.9 mm. At a longitudinal position defined by a specific length, the head portion preferably exhibits a second diameter ($d_2$) in the range of 7.5 mm to 9.5 mm, preferably 8 mm to 9 mm, further preferred 8.3 mm to 8.8 mm especially 8.5 mm. Preferably, the ratio of these diameters ($d_1:d_2$) is in the range of 0.57 to 0.65, especially about 0.58 or about 0.63. Such a shape can ensure that the head portion is blocked well before reaching the eardrum. Preferably, the specific length is in the range of 18 mm to 22 mm, more preferable 19 mm to 21 mm, especially 20 mm. These diameters or ratios can ensure that the head portion, especially the distal end, exhibits geometrical dimensions ensuring that the head portion can be introduced only in the area of soft connective tissue confining an outer ear canal of the patient's outer ear, but not in the area of hard bone confining the outer ear canal. Such a shape can ensure that the otoscope can be applied by laypersons without the risk of irritations of the tissue.

Preferably, the probe cover exhibits a shape or an inner contour which geometrically corresponds with the shape of the head portion. In particular, the probe cover exhibits the same shape as the head portion, as describes above. A wall thickness of the probe cover preferably is in the range of 0.02 mm to 0.05 mm. Therefore, an outer shape or contour of the probe cover can be characterized by the measurements stated with respect to the head portion, adding 0.04 to 0.1 mm in diameter.

The head portion and/or the handle portion may exhibit fixation means for fixing a probe cover at the otoscope. Thereby, a probe cover can be fixed at the head portion or handle portion such that relative motion can be prevented. Such fixations means can prevent premature unfolding of the probe cover, as relative motion between the head portion and a probe cover is only enabled at a time when the distal tip is introduced far enough. The risk of ear wax obstructing visual communication can be minimized.

Further, the otoscope may comprise at least one light source positioned at the distal end, especially at the distal tip, the moving mechanism being configured to move the probe cover with respect to the at least one light source. Such a moving mechanism allows for displacing any objects, e.g. ear wax, away from an illumination point, especially a favorable eccentric illumination point. Preferably the at least one light source is positioned radially offset from the longitudinal axis.

The term "light source" is understood to apply to any source emitting photons. A light source positioned at the distal end or tip ensures illumination of the ear canal, even in case the distal tip is only introduced as deep as a transition area between the two types of tissue. Distal eccentric light sources facilitate realization of the concept of "looking around the corner".

Since geometrical restrictions limit the space at the distal end of the head portion, the light source is preferably formed by the distal end of a light guide. For example, the light guide may exhibit a diameter of less than 1 mm, preferably of less than 0.5 mm, more preferably of about 0.2 mm. The light guide may be connected to an LED located remote from the distal end of the head portion. The light guide may be e.g. a nylon light guide, preferably having a diameter of only about 0.2 mm to 1 mm. Alternatively, a light source may be formed e.g. by a small light emitting diode (LED) that is placed directly at the distal end of the head portion. The LED can ensure illumination with low energy consumption and minimum generation of heat.

The light guide can be made of polymethyl methacrylate (PMMA) or polyamide, especially polyamide 6.6. PMMA provides the advantage of good optical characteristics. Polyamide 6.6 provides the advantage of high flexibility.

The light guide may allow placement of the light source at a distance from the distal end with less spatial constrains and space for means (e.g. a printed circuit board) for effective heat dissipation. Such an arrangement facilitates realization of the concept of "looking around the corner", especially as the light guides may be arranged with a maximum radial offset without any risk of thermally damaging tissue. Effective heat dissipation reduces the impact of the otoscope on the tissue confining the ear canal, avoiding thermal irritation of the tissue.

It is advantageous, if the otoscope comprises a plurality of light sources at the distal end of the head portion, preferably with each light source being separately controllable. Thereby, the ear canal can be illuminated from a favorable eccentric illumination point, reducing e.g. shadowing. Also, by illuminating objects in the patient's ear canal from different positions, e.g. by sequentially switching on and off the individual light sources, it may also be envisaged to distinguish different objects in the ear, without necessarily having to displace the electronic imaging unit by a motion mechanism within the ear canal. An object relatively far away from the electronic imaging unit, such as the eardrum, will change its appearance only slightly when being illuminated from different positions at the distal end of the head portion. However, artifacts that are relatively close to the electronic imaging unit (such as hair and earwax) will change their appearance (position) drastically. The otoscope therefore preferably comprises means, in particular a logic unit, such as a microprocessor, configured to distinguish different objects in the patient's ear based on images taken with the objects being illuminated from different positions.

Preferably, a logic unit is coupled with at least two of the light sources and is arranged for individually switching on and off the light sources and/or for individually varying the light intensity. Additionally or alternatively, the at least one light source may be controllable in view of the color, so that it is possible to change the color of the light emitted by the light source. For example red color may be preferred to recognize an inflamed eardrum, wherein green color may be preferred to recognize earwax.

The otoscope may comprises a logic unit which is coupled with at least two of the light sources and is arranged for individually switching on and off the light sources and/or for individually varying the light intensity. Individually switching on and off enables stereoscopic viewing, especially depth analysis along the optical axes due to changes in reflected light patterns. Also, segmented lighting of the ear canal can be carried out. For example, three light sources each illuminate a specific portion of the ear canal. Feedback regulation of each of the light sources allows for homogeneous illumination of the ear canal, especially based on different illumination levels. Preferably, a logic unit is coupled to each of the light sources, the logic unit allowing for feedback regulation and/or adjustment of illumination levels.

Like the electronic imaging unit, the at least one light source is preferably positioned radially offset from the longitudinal axis of the head portion. Such a configuration allows illumination of the eardrum without the need to introduce the light source as deeply into the ear canal as it would be necessary, if the light source were placed centrally on the longitudinal axis of the head portion. The offset may be at least 1 mm, preferably at least 1.5 mm, more preferably at least 2 mm from the longitudinal axis. Preferably, the offset is maximum with respect to the confines of the outer diameter of the head portion. According to one embodiment, the offset is in the same range as a radial offset of the at least one optical axis. According to one embodiment, the radial offset of the at least one light source is as large as a radial offset of a camera of the electronic imaging unit. Such an arrangement is favorable in order to observe the entire eardrum or in order to reduce shadowing.

According to one embodiment, the moving mechanism is configured for automatically initiating relative displacement of the probe cover based on mechanical reaction forces exerted by the probe cover on the moving mechanism. Such a moving mechanism enables adequate use by laypersons, even in case a layperson is not aware of appropriate handling of the otoscope. In particular, with such a mechanism, the probe cover can be displaced at a time when the head portion is blocked in an end position within the ear canal, especially at a transition area between soft connective tissue and hard bone.

According to one embodiment, the moving mechanism comprises an adapter which is arranged to axially position the probe cover in at least one specific axial position relative to the head portion. A predefined axial position allows for providing a probe cover reservoir which is not unfolded unintentionally during insertion of the head portion. The adapter preferably exhibits fixing means for connecting the probe cover to the adapter. The fixing means may be provided in the form of e.g. a clip mechanism and/or any protruding portion. Preferably, the fixing means are adjustable manually in an easy way, in order to facilitate repetitive fixation of disposable probe covers.

According to one embodiment, the adapter is arranged to axially position the probe cover in a first starting position, in which the probe cover can (manually) be coupled to the otoscope, and in a second end position, in which a/the reservoir of the probe cover is displaced relative to the distal end of the head portion. Predefined axial positions, which can be modified, allow for displacing the probe cover about a predefined distance, especially only at a time when the electronic imaging unit is in visual communication with the eardrum. A predefined second axial position allows for determining a specific compressive stress or force or a specific tension, especially tensile stress, which is transferred to the probe cover, especially for homogeneously stretching a reservoir of the probe cover.

According to one embodiment, the adapter exhibits fixing means adapted for engaging an inner lateral surface section of the probe cover. Engaging an inner lateral surface section of the probe cover can ensure reliable or secure connection between the fixing means and the probe cover, even in case relatively high forces have to be exerted on the probe cover. Reliable connection between the fixing means and the probe cover can be ensured even in case the probe cover is provided with very low inherent stability only.

According to one embodiment, the adapter exhibits fixing means adapted for engaging the probe cover along a lateral surface completely in a circumferential direction, especially section by section or along the whole circumference. Thereby, the distal tip or portion of the probe cover can be stretched homogeneously, which may ensure that any line of sight or any of a plurality of radially offset optical axes is not obstructed. Also, relative motion between the probe cover and the head portion may be maximum at any point of the distal tip which is positioned radially offset.

According to one embodiment, the moving mechanism comprises both an adapter which is movably mounted, especially axially movably mounted, and a moving device cooperating with the adapter. The moving device can provide a reaction force, especially in order to determine a threshold value for an axial force which has to be exceeded in order to axially displace the probe cover. This allows for displacing the probe cover only at a time when the distal tip of the head portion is positioned at a transition point or area between soft connective tissue and hard bone confining the ear canal, i.e. at a time when the electronic imaging unit is in visual communication with the eardrum. The moving device preferably defines a first position of the adapter, the first position corresponding to a starting position in which the probe cover and the adapter haven not been moved or displaced yet. The starting position can be defined in conjunction with any mechanical end stop or limit stop which may be provided by the head portion.

According to one embodiment, the adapter is arranged for axially guiding a probe cover along the head portion, especially along a predefined translational axis. This enables a moving mechanism which is not likely to cant or to displace the head portion out of a favorable position within the ear canal.

According to one embodiment, the moving mechanism comprises a moving device which is arranged to exert a reaction force on the adapter, especially in a distal axial direction. This allows for displacing the probe cover only at a specific time, depending on the amount of the reaction force, especially at a time when the electronic imaging unit is in visual communication with the eardrum. Preferably, the moving device is prestressed or elastically preloaded in a direction substantially parallel to the longitudinal axis of the head portion, and the moving device is arranged for positioning the adapter at the mechanical end stop or limit stop.

According to one embodiment, the moving mechanism is arranged to define a threshold value for an axial force exerted on the moving mechanism in the proximal direction. This allows for displacing the probe cover only at a specific time, depending on the amount of the reaction force, especially at a time when the electronic imaging unit is in visual communication with the eardrum. In particular, the threshold value can be defined in dependence on the shape of the head portion. The head portion is shaped such that it can be introduced only as deep as a transition area between soft connective tissue and hard bone. Thus, once the head portion is mechanically blocked within the ear canal, an axial force exerted on the moving mechanism increases, and any latch mechanism of the moving mechanism can be released.

According to one embodiment, the moving mechanism comprises a motion sensor which is connected to the imaging unit and/or to at least one light source and/or to a logic unit of the otoscope, the motion sensor being configured to detect a motion of the moving mechanism and/or of the probe cover relative to the head portion. Such a motion sensor allows for switching on the respective component only at a time when the probability is increased that the electronic imaging unit is in visual communication with the eardrum, i.e. when the electronic imaging unit and the eardrum are arranged on one line of sight.

According to one embodiment, the moving mechanism comprises force detection means. Detecting the force exerted on the probe cover or on the head portion allows for controlling or adjusting an appropriate instant of time for relatively moving the probe cover, especially automatically, such that the use of the otoscope is easy to understand for laypersons. In particular, the layperson does not have to decide whether or when the probe cover has to be moved or unfolded.

When introducing the tip end of the head portion no deeper into the ear canal than to the border between the outer part and the inner part of the outer ear canal of the patient's outer ear, i.e. to a transition area between the two types of tissue, there is the risk that artifacts, such as earwax, hair and other kind of dirt from the outer part of the outer ear canal obstruct the view of the small electronic imaging unit onto the patient's eardrum. Therefore, it is advantageous to take several images from different positions within the ear canal. For doing so, the otoscope according to the present invention may comprise more than one optical axis or cameras at the distal end of its head portion, e.g. two optical axis or cameras, located at different positions on the head portion.

In another preferred embodiment, the otoscope according to the present invention further comprises a motion mechanism configured to allow displacement of the electronic imaging unit or at least one optical axis of the electronic imaging unit relative to the handle portion. With such a motion mechanism, it is possible to position the at least one optical axis in a favorable eccentric observation point, substantially irrespective of the position of the head portion within the ear canal. Also, with such a motion mechanism, it is possible to capture a plurality of images from different positions from one optical axis within the patient's ear canal, thereby avoiding the need for two or more cameras or the need for beam splitter optics. With a motion mechanism, a plurality of favorable eccentric observation points can be realized, although there may be only one single optical axis. If, for example, a hair—at least partially—obstructs the view of the electronic imaging unit at a certain position within the ear canal onto the eardrum, the electronic imaging unit may have a free view onto the eardrum at another position in the ear canal or may at least have a free view onto the part of the eardrum that was partially obstructed by the hair before.

It has been found that positioning the at least one optical axis radially offset induces or brings about that the eccentric observation point positioned at the distal tip on this least one optical axis may be positioned at an unfavorable position, e.g. adjacent to a section of the ear canal having a minimal radius of curvature. Therefore, departing from at least one a radially offset optical axis, the motion mechanism may facilitate to make the concept of "looking around the corner" more practicable.

Moreover, providing such a motion mechanism also allows for automatic identification of different objects in the patient's ear. Usually, in otoscopy, the eardrum represents the object of primary interest. In contrast, artifacts, such as earwax, hair and other kind of dirt, are usually of no particular interest. Such artifacts rather represent a problem when obstructing the view onto the patient's eardrum.

However, since artifacts are relatively close in front of the electronic imaging unit in the ear canal, compared to the eardrum, the artifacts can be distinguished from the eardrum when displacing the electronic imaging unit within the ear canal. That is, artifacts are depicted at distinct positions, if two images are captured from different positions/perspectives within the ear canal (due to their short distance to the electronic imaging unit), whereas the eardrum is shown substantially at the same position (due to the relatively large distance to the electronic imaging unit). According to the principle of stereoscopic viewing, the inventive device enables to determine the distance of different objects with respect to the electronic imaging unit. This determination can be automatically calculated by means of a logic unit, such as a microprocessor, preferably forming part of the otoscope. Furthermore, objects that have been identified as artifacts (due to their close distance to the electronic imaging unit) may be (automatically) eliminated by the image processing unit by comparing two or more images captured from different positions within the patient's ear canal. Consequently, a superimposed image may be generated or calculated by image processing means eliminating the artifacts. The image processing means may be implemented in form of a logic unit, such as a microprocessor provided in the otoscope. Thus, an image clearly depicting the eardrum can be obtained, even if the tip end of the head portion is introduced into the ear canal to the border between the outer part and the inner part of the outer ear canal (and not deeper into the ear canal).

The motion mechanism is preferably configured to allow at least partial rotation of the electronic imaging unit or the at least one optical axis about an axis of rotation. The axis of rotation may correspond to the longitudinal axis of the head portion. By displacing the electronic imaging unit along a predefined motion path, it is possible to automatically calculate the distance of the electronic imaging unit to the detected objects, as described above. In view of the typical size of the artifacts found in the ear canal, such as hair and earwax particles, the motion mechanism preferably allows for displacement of the optical axis of at least 1 mm, more preferable at least 2 mm, further preferred at least 3 mm, within the patient's ear canal. For example, in case a radial offset of 1.8 mm or 2 mm is realized, a rotation of 90° evokes a displacement of about 3 mm. A rotation of at least 90°, more preferably of at least 120°, even more preferably of 180° or even more degrees around the axis may be realized. In conjunction with an electronic imaging unit exhibiting two optical axes or comprising two cameras, a rotation of maximum 90° may be adequate in order to find the most favorable eccentric observation point. In conjunction with an electronic imaging unit exhibiting three optical axes or comprising three cameras, a rotation of maximum 60° or 70° may be adequate. Preferably, the motion mechanism allows for rotation in both directions, i.e. clockwise and counter-clockwise. The motion mechanism may also allow for rotational displacement about more than one axis. The motion mechanism may comprise at least one motor and one or more gears and/or bearings. The electronic imaging unit may be connected to a flexible cable, e.g. a flexible ribbon cable, to allow for such a movement.

Preferably, the probe cover is adapted to be fixed to at least one section of either the head portion and/or the handle portion in such a way that the probe cover does not move relative to the handle portion during displacement of the electronic imaging unit or the at least one optical axis or at least one camera by the motion mechanism. Otherwise, artifacts, such as earwax particles, adhering to the probe cover will be depicted by the electronic imaging unit, even if the electronic imaging unit is displaced by the motion mechanism. This, however, would interfere with object identification and elimination of artifacts from the captured images.

Preferably, the at least one light source is arranged so as to maintain a predetermined distance with respect to the electronic imaging unit or the at least one optical axis, even when the electronic imaging unit or the at least one optical axis is displaced by the motion mechanism. Such a configuration is advantageous, because the predetermined distal relationship between the at least one light source and the optical axis allows for improved (automatic) image analysis. If a motion mechanism is provided, the motion mechanism preferably also displaces the at least one light source. If the light source is provided in the form of a light guide, the light guide should be sufficiently flexible to allow for such a displacement of the at least one light source. Preferably, the light guide is fixed distally within the head portion, wherein the light guide is elastic, the elasticity allowing for bending and/or twisting. Alternatively, the light guide may be rigid, wherein the entire lightning apparatus may be displaced in conjunction with the head portion.

According to one embodiment, the at least one light source is coupled with the motion mechanism, especially directly or via the electronic imaging unit, such that the motion mechanism allows for at least partial rotation of the at least one light source about an axis of rotation, wherein the axis of rotation preferably corresponds to the longitudinal axis. Rotating the light source in a favorable position can allow for observing the entire eardrum with a high reliability.

According to one embodiment, the head portion and/or the handle portion exhibits a form-fit shape which provides a coupling for fixing the probe cover to the otoscope such that it does not move during displacement of the electronic imaging unit or the at least one optical axis or at least one camera by the motion mechanism. The form-fit shape can ensure that artifacts, such as earwax particles, adhering to the probe cover will not be depicted by the electronic imaging unit when the electronic imaging unit is displaced by the motion mechanism. Preferably, the form-fit shape is provided on an outer surface of the head portion or the handle portion.

Preferably, an optical component of the electronic imaging unit or at least one optical axis of the electronic imaging unit or at least one camera is tilted against the axis of rotation so as to be continuously directed to a predetermined point on the axis of rotation, the predetermined point having a fixed distance to the electronic imaging unit or to the camera. In view of the typical length of the inner part of the outer ear canal of the patient's outer ear, the distance may be between 3 mm and 20 mm, preferably between 10 mm and 15 mm. Thus, the "viewing direction" of the electronic imaging unit is optimized for centering on the eardrum, which usually represents the object of primary interest within the patient's ear.

The above mentioned object is achieved according to the present invention by a probe cover adapted to be put over the head portion of an otoscope according to the invention, wherein at a distal end, the probe cover exhibits a reservoir which allows for modifying the shape of the probe cover, especially the shape of a distal end of the probe cover, in order to move the probe cover with respect to the head portion. In particular, the reservoir allows for displacing the probe cover from a first position, in which the probe cover is coupled to the otoscope, to a second position, in which the reservoir is displaced relative to a distal end of the head portion, when a force, especially a pulling force, is exerted on the probe cover. Preferably, at least partially, the reservoir is a folded film or foil portion which can be unfolded when exerting a pulling force on the probe cover. Such a reservoir, especially a folded film or foil reservoir, enables to displace any artifact out of the field of vision of the electronic imaging unit, especially by axially pulling the probe cover in a proximal direction. Alternatively or in addition, the reservoir may be provided by a portion which is more ductile or stretchy or tensile or elastic than other portions or sections of the probe cover, at least partially.

Preferably, the probe cover is designed in a way that allows unfolding or peeling of portions of the probe cover in order to move portions of the probe cover contaminated e.g. with earwax away from the electronic imaging unit. The otoscope preferably contains mechanical means to move the probe cover against the electronic imaging unit or vice versa.

According to one embodiment, the reservoir is provided by a portion of the probe cover which is arranged centrally at a distal tip of the probe cover, or by a portion of the probe cover which annularly overlaps an outer section of a distal tip of the probe cover, or by a plurality of concentric circular bends provided at a distal tip of the probe cover. Each of these embodiments provides an arrangement which can ensure that any artifacts can be effectively displaced out (radially) away from an observation point at the distal tip of the head portion, especially a favorable eccentric observation point. In particular, annularly overlapping sections and/or a plurality of concentric circular bends provided at a distal tip provides the advantage that there is no need for a groove, recess or cavity at the distal tip of the head portion for accommodating the reservoir. Rather, a further sensor, e.g. an infrared sensor unit, may be arranged directly at the distal tip, especially centrically.

A distal tip of the probe cover may be conceived as a front face or front side of the probe cover.

According to one embodiment, at a proximal end, the probe cover exhibits a protrusion which is arranged for axially position the probe cover with respect to the head portion. A predefined axial position, which can be modified, enables to displace the probe cover only at a time when the electronic imaging unit is in visual communication with the eardrum.

According to one embodiment, the probe cover is a double-ply probe cover. A double-ply probe cover provides high structural stability, even if the probe cover is made by deep-drawing. Preferably, the distal foil portion covering the camera is very thin and transparent, exhibiting a wall thickness of e.g. 30 micrometer (µm) to 50 micrometer, especially 20 micrometer.

According to one embodiment, the reservoir is provided by an inner shell of the double-ply probe cover. This design can ensure that the reservoir can be covered by an outer shell of the probe cover, at least partially. Thus, any artifacts can be kept away from the inner shell more effectively. Also, any contact of the reservoir with an inner lateral surface of the ear canal can be avoided or prevented, preventing premature unfolding of the reservoir.

According to one embodiment, the probe cover is a double-ply probe cover, wherein at least one gap or groove between shells of the probe cover provides a gas conduit, especially an air channel into the ear canal during examination. This allows for pressurizing the eardrum.

According to one embodiment, the probe cover exhibits two shells which both provide a form-fit protrusion, especially a U-shaped rim, adapted for interlocking with the probe cover moving mechanism, wherein the protrusions lie on top of each other. Alternatively or in addition, the probe cover may exhibit two shells which are bound together at the proximal end by welding, e.g. ultrasonic welding, or by gluing. Such a design can ensure that both shells are displaceable by a moving mechanism, preventing that one of the shells is displaced relative to the other, which eventually could cause twisting or distortion of the probe cover.

According to one embodiment, at a distal tip, the probe cover exhibits an opening and/or a predetermined breaking or unfolding point. Such a design enables displacement of the respective section of the probe cover, especially of an outer shell of the probe cover, out of the field of vision, especially at a time when the electronic imaging unit is in visual communication with the eardrum.

According to one embodiment, the probe cover is a molded plastic, especially made by deep-drawing or thermoforming, wherein the material of the probe cover preferably is polypropylene. Such a probe cover can easily be provided as a disposable, especially in a cost-effective way. Thus, laypersons do not have to clean or sterilize any component of the otoscope. Also, such a probe cover can exhibit an adequate stiffness, in order to prevent twisting or any distortion of the probe cover during insertion of the head portion into the ear canal. Also, such a probe cover can exhibit an adequate stiffness allowing for transferring an axial reaction force to the moving mechanism, in order to initiate displacement of the probe cover only when a specific threshold value of a force exerted on the probe cover or head portion is exceeded. In other words: The material or the stiffness is provided such that displacing the probe cover can be initiated automatically based on mechanical reaction forces, and does not occur prematurely during insertion of the otoscope into the ear canal.

According to one embodiment, in a distal direction, the probe cover exhibits a decreasing wall thickness towards the distal end, especially decreasing at least by half, or decreasing by 1/10 to 1/20. On the one hand, such a taper can ensure adequate stiffness of a proximal portion of the probe cover, especially of a portion which is provided for transferring axial forces to the otoscope. On the other hand, a relatively low wall thickness at the distal tip can facilitate unfolding. The wall thickness or the tapering preferably is in the range between 10 micrometer and 100 micrometer, further preferred between 5 micrometer and 70 micrometer, especially between 20 micrometer and 50 micrometer.

According to one embodiment, the probe cover is adapted to be fixed to at least one portion of the head portion and/or the handle portion of the otoscope in such a way that the probe cover does not move relative to the handle portion during rotation of the electronic imaging unit or the at least one optical axis.

According to one embodiment, at a proximal end, the probe cover exhibits a collar, especially a radially protruding discoid collar, which is arranged for fixing the probe cover at a stationary portion of the head portion and/or at the handle portion. A collar can ensure exact positioning of the probe cover with respect to the handle portion or the head portion. The collar may also provide a stiff handle area to manually mount the probe cover on the otoscope. Also, the collar can protect the handle portion from any body fluids. Thus, laypersons do not have to clean or sterilize any component of the otoscope.

According to one embodiment, the otoscope further comprises an infrared sensor unit positioned at the distal end of the head portion, especially at a distal tip of the head portion, especially centrically. The infrared sensor unit may be provided as a component of the electronic imaging unit, or as a separate sensor unit. Providing an otoscope comprising an infrared sensor unit for temperature detection in conjunction with an optical identification of objects allows for more reliable identification of the objects, e.g. of the eardrum. Providing an otoscope additionally with an infrared sensor unit allows for minimizing any risk of misdiagnosis. Pre-diagnosis may be facilitated. Temperature detection may assist a physician in carrying out diagnosis. Any more advanced or final disease diagnosis has to be carried out by the physician on the basis of other symptoms exhibited by the subject, which are observed by the physician, or by the physician's further examination.

The infrared sensor unit may be connected to a logic unit, the logic unit being configured for processing data from both the infrared sensor unit and the electronic imaging unit, especially simultaneously. Data acquired by the infrared sensor unit can be verified based on data acquired by the electronic imaging unit, and vice versa. The infrared sensor unit can be provided at same positions like positions discussed in context with the electronic imaging unit or the light sources. Likewise, the infrared sensor unit can be displaced in the same manner as discussed in context with the electronic imaging unit or the light sources.

The otoscope may further comprise a logic unit, such as a microprocessor. The logic unit may be configured to control the electronic imaging unit and/or the at least one light source and/or an infrared sensor unit. The logic unit may analyze the images obtained by the electronic imaging unit e.g. in order to detect an inflammation of the eardrum and/or the inner part of the outer ear canal, and/or in order to compare two images obtained with the electronic imaging unit located at different positions within the ear and/or with the object illuminated from different positions, so as to identify and discriminate different objects in the patient's ear. The logic unit may further be configured to generate or calculate a new image wherein predetermined objects that have been previously identified are eliminated.

The above mentioned object is achieved according to the present invention by an ear inspection device, comprising an otoscope according to any one of the embodiments of the present invention, further comprising a probe cover according to any one of the embodiments of the present invention. For example, the ear inspection device can be provided as a kit or assembly, including e.g. a plurality of disposable probe covers, or the ear inspection device can be provided with the probe cover mounted at or fitted onto the head portion.

According to one particular embodiment, the above mentioned object is achieved according to the present invention by a method of identifying objects in a subject's ear, wherein the method comprises the following steps:

introducing a head portion of an otoscope in conjunction with an at least partially transparent probe cover put over the head portion into an ear canal of a subject's outer ear, the head portion accommodating an optical electronic imaging unit which exhibits at least one optical axis;

moving at least a portion of the probe cover with respect to the at least one optical axis, especially automatically, e.g. by a motor or by a mechanical latch mechanism or against an axial force of an elastic element; and using the electronic imaging unit to capture at least one image.

The step of relatively moving at least a portion of the probe cover may be initiated, especially automatically initiated, in dependence on a force exerted on the probe cover or the head portion, wherein the force may be detected by a force sensor accommodated within the head portion or the handle portion of the otoscope. Alternatively, the step of relatively moving at least a portion of the probe cover may be initiated mechanically, especially by a pretensioned or preloaded compression spring which is compressed only when the (axial) force exerted on the probe cover or the head portion exceeds a threshold value.

The step of relatively moving at least a portion of the probe cover may comprise axially displacing a proximal end of the probe cover with respect to the head portions and radially displacing a distal tip of the probe cover with respect to the distal tip or front side of the head portion. This may effectively displace ear wax or any other object adhering the probe cover.

The method may further comprise the step of using the electronic imaging unit to capture a plurality of images from an observation point arranged on the at least one optical axis, especially from a plurality of different eccentric observation points.

According to one particular embodiment, the above mentioned object is achieved according to the present invention by a method of identifying and medically characterizing the eardrum in a subject's ear, characterized in that the method comprises the following steps:

introducing a head portion of an otoscope in conjunction with an at least partially transparent probe cover, which is put over the head portion, into an ear canal of a subject's outer ear, the head portion accommodating an optical electronic imaging unit which exhibits at least one optical axis;

detecting a force exerted on the head portion or the probe cover during introduction, especially a force in a direction substantially parallel to a longitudinal axis of the head portion; and moving at least a portion of the probe cover with respect to the at least one optical axis, especially in dependence on a specific threshold value of a detected force;

using the electronic imaging unit (40) to capture at least one image of the eardrum; and evaluating a medical condition of the eardrum by medically characterizing the eardrum based on at least one image captured of the eardrum, in order to provide medical evidence of the eardrum.

Medically characterizing the eardrum preferably is carried out automatically by the device, especially based on predefined ranges, e.g. with respect to temperature or a specific degree of reddishness. In other words: Medically characterizing the eardrum comprises at least one step of automatically evaluating the imaged captured by the electronic imaging unit, especially by means of a logic unit, e.g. based on one of the characteristics of the eardrum described above.

Such a method may provide a layperson with a diagnosis, especially a pre-diagnosis, substantially irrespective of any skills of the layperson, in particular substantially irrespective of the position of the head portion within the ear canal. In other words: the otoscope is configured for reliably providing the layperson with medical information, e.g. in order to facilitate any decision whether a physician should be visited. Thereby, capturing images in dependence on a specific force enables evaluation of images which show the eardrum with high reliability. Misdiagnosis may be precluded more effectively, even when the method or the otoscope is applied by laypersons.

The method may comprises the step of using an infrared sensor unit for detecting the temperature of the objects, the infrared sensor unit preferably being positioned at a distal end of the head portion. Detecting the eardrum's temperature may facilitate diagnosis and may further facilitate to provide a layperson with medical information, without the need of visiting a physician.

DESCRIPTION OF THE FIGURES

Exemplary embodiments of the present invention will be described in more detail in the following with respect to the drawings, wherein:

FIG. 1 schematically shows a cross-sectional view of a head portion and of a part of a handle portion of an embodiment of an otoscope according to the present invention;

FIG. 2 shows an enlarged view of a plate covering a bore provided in the head portion illustrated in FIG. 1;

FIGS. 9A to 9F schematically show cross-sectional views of alternative embodiments of a probe cover arranged on a head portion of a further embodiment of an otoscope according to the present invention, the probe cover being positioned in a first or second position;

In case any reference sign is not explicitly described in a respective figure, it is referred to the other figures. In other words: Like reference characters refer to the same parts or the same type or group of device throughout the different views.

DESCRIPTION OF PREFERRED EMBODIMENTS

Figure 3:
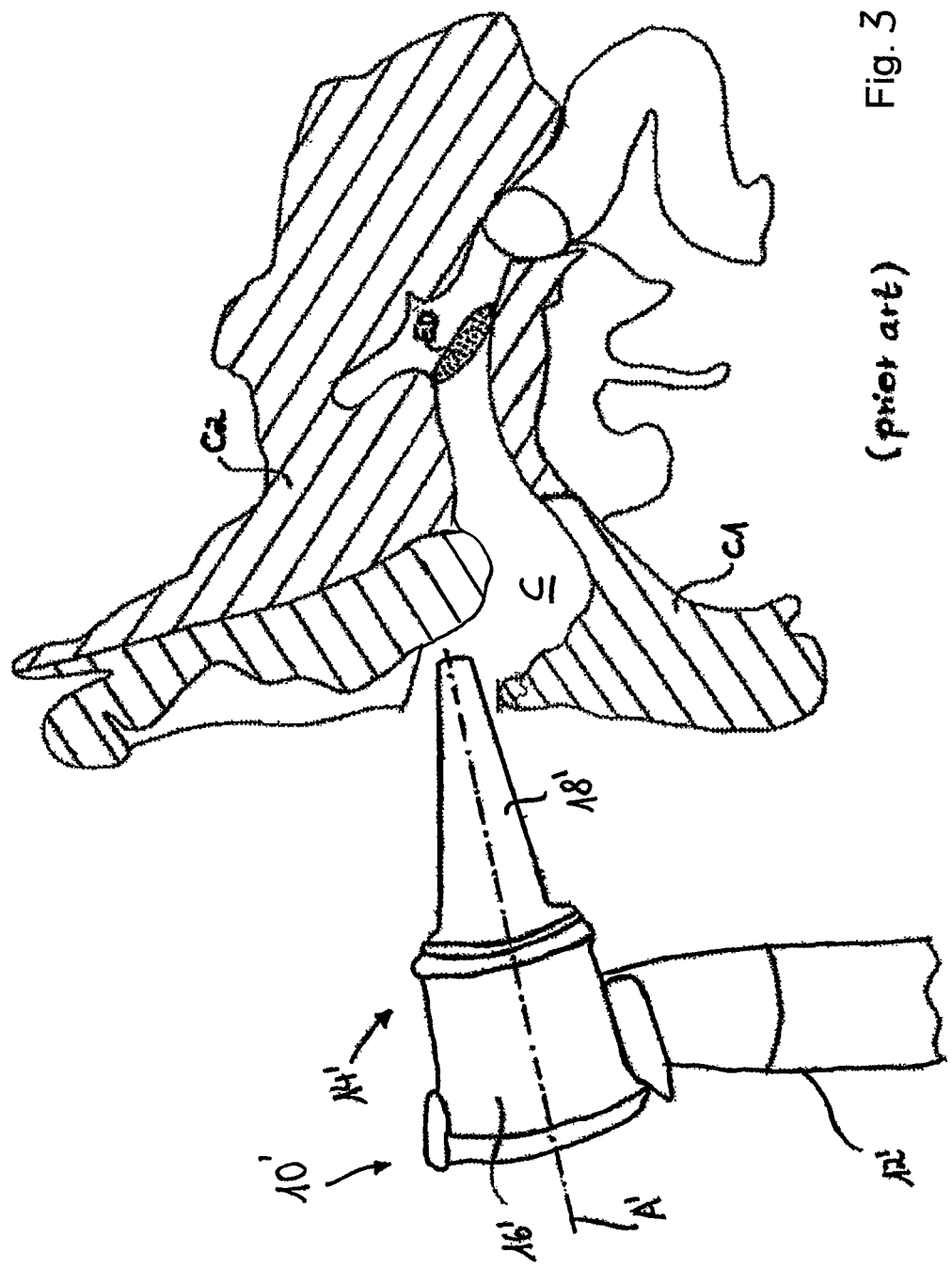
FIG. 3 shows an otoscope of the prior art, with its head portion partially introduced into the patient's ear canal.
Figure 4:
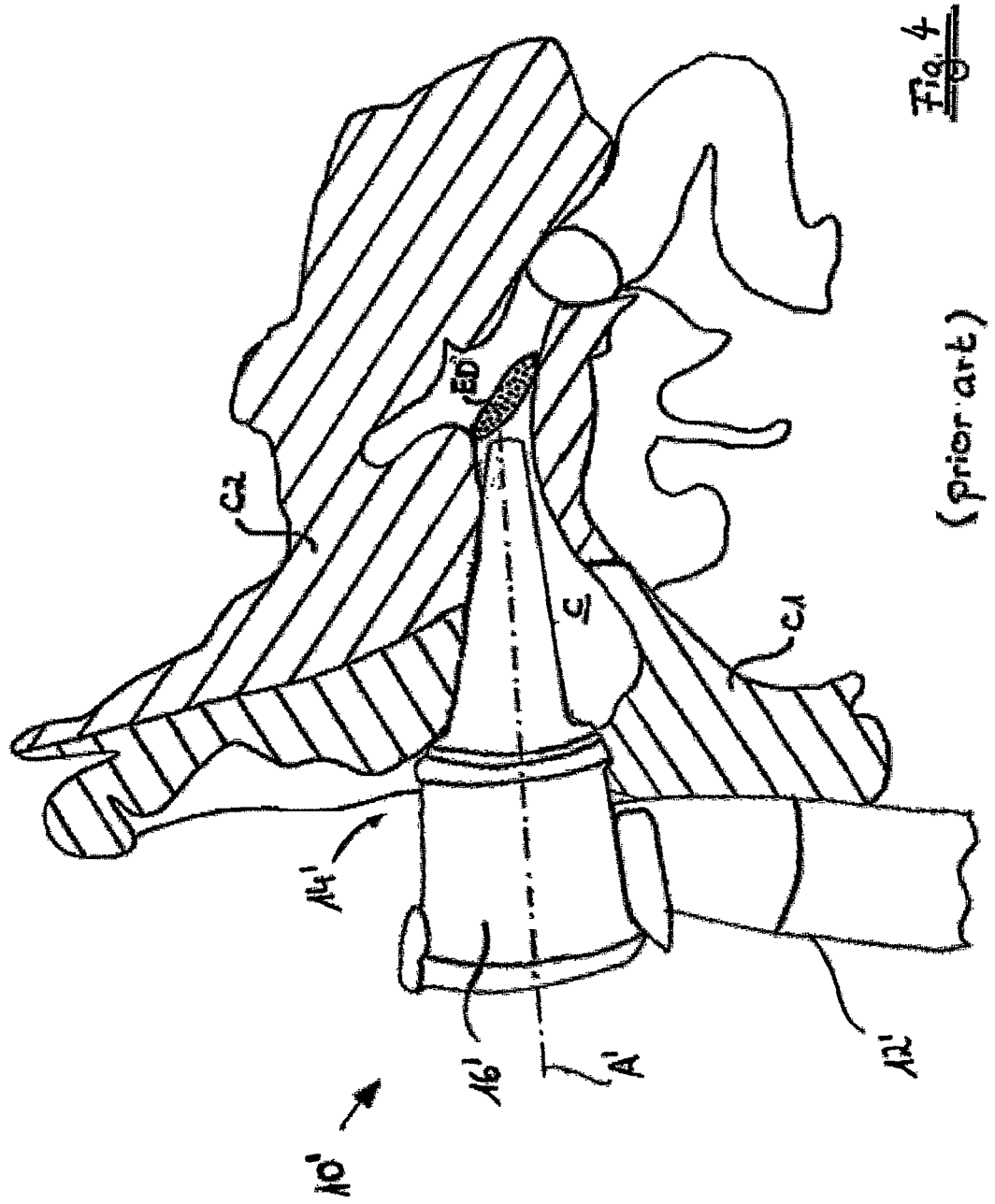
FIG. 4 shows the otoscope of FIG. 3 with its head portion fully introduced into the subject's ear canal.

FIG. 1 schematically shows a cross-sectional view of a head portion 14 and a part of a handle portion 12 (only shown in phantom lines) of an embodiment of an otoscope 10 according to the present invention. As can be seen from FIG. 1, the head portion 14 has a substantially tapering form extending along a longitudinal axis A of the head portion 14. The head portion 14 comprises a relatively large proximal end 16 adjacent to the handle portion 12 and a smaller distal end 18. The distal end 18 of the head portion 14 is adapted to be introduced into a patient's ear canal.

Furthermore, the head portion 14 comprises a rotatable, radial inner portion 20 and a fixed, radial exterior portion 22. The rotatable portion 20 is rotatable about an axis of rotation R which—in the shown exemplary embodiment—corresponds to the longitudinal axis A of the head portion 14. A motion mechanism 24 comprising a servo motor 26 is positioned within the handle portion 12 and is coupled to the rotatable portion 20 of the head portion 14, so as to rotate the rotatable portion 20 about its axis of rotation R relative to the fixed portion 22 of the head portion and relative to the handle portion 12 of the otoscope 10. The rotatable portion 20 is supported by a radial bearing 28 (also only schematically shown).

In the shown exemplary embodiment, the exterior portion 22 of the head portion 14 comprises a support structure 30 providing the required stability to the head portion 14. The support structure is at least partially covered by an outer cladding 32 formed from a relatively soft material, such as silicone. The cladding 32 makes it more comfortable for the patient to introduce the distal end 18 of the head portion 14 into his ear canal. The cladding may comprise a circular slot-like recess 33 adapted to engage with a complementarily formed circular tongue of a (not shown) probe cover. The probe cover may be formed from a plastic material and may be adapted to be put over the head portion 14. Preferably, the probe cover is formed from a transparent material. Its wall may be relatively thin, thereby making the probe cover relatively flexible. At least a portion of the probe cover covering the distal end 18 of the head portion 14 should be transparent, so as to allow an electronic imaging unit (described in the following) which is located at the distal end 18 of the head portion 14 to have a free view through the probe cover. For hygienic reasons, the probe cover is preferably designed as a single-use product. The probe cover also reliably inhibits contamination of the distal end 18 comprising the electronic imaging unit. Without such a probe cover there is a high risk that e.g. earwax particles may adhere to the electronic imaging unit (thereby deteriorating the image quality thereof) when introducing the distal end 18 into the outer part of the outer ear canal of the patient.

The head portion 14 comprises a distal end point 34 which, in the shown exemplary embodiment, is located substantially on the longitudinal axis A of the head portion 14. However, the head portion 14 might alternatively have a tapering shape that is not substantially symmetrical to its longitudinal axis A (as shown in FIG. 1) but is more adapted to the anatomy of the human ear canal.

Irrespective of the precise shape of the head portion 14, the head portion 14 is preferably dimensioned in such a way that it cannot be introduced into the inner part of the outer ear canal of the patient's outer ear. In the shown exemplary embodiment, the distal end 18 of the head portion 14 has a substantially round shape. Only a few millimeters (less than 4 mm) away from the distal end point 34 in the direction of the longitudinal axis A, the head portion 14 exhibits a diameter of more than 5 mm. Since the inner part of the outer ear canal of an adult usually exhibits a diameter of 4 mm, there is no risk that the distal end 18 of the head portion 14 is inadvertently introduced too deeply into the patient's ear canal. Therefore, injuries to the sensitive skin of the inner part of the outer ear canal and/or to the eardrum can be reliably avoided.

The movable portion 20 comprises a bore 36 or a tubing extending substantially along the axial direction A of the head portion 14, but not exactly parallel thereto. The distal end of the bore 36 is located in proximity to the distal end point 34, but offset with its bore axis B by at least 2 mm from the longitudinal axis A. Furthermore, the distal end of the bore 36 is closed by a plate 38. An enlarged top view of the plate 38 is shown in FIG. 2. Since the bore 36 is cylindrical in shape, the plate 38 has a generally circular appearance in FIG. 2 with the bore axis B forming the center thereof. However, the bore 30 and/or the plate 38 may equally exhibit other shapes.

The plate 38 supports an electronic imaging unit 40 comprising a wide-angle color video camera 40.1 and distal ends of four light guides 42. In the exemplary embodiment, the light guides 42 are located around the electronic imaging unit 40 or camera 40.1, such that one light guide 42 is associated to each of the four lateral sides of the substantially rectangular electronic imaging unit 40 or camera 40.1. However, this is not a prerequisite for the present invention. Instead of four light guides 42, for example, only two or three light guides 42 may be provided in the otoscope 10. The electronic imaging unit 40 comprises advantageously a wafer-level camera of dimensions in the 1 to 2 mm range having a substantially flat configuration. The wafer-level camera advantageously exhibits dimensions of only about 1 mm×1 mm providing a resolution of about 250 pixels of 250 pixels. The plate 38 has a diameter between 1.5 mm and 2.0 mm and the light guides 42 have a diameter of only about 0.2 mm.

The video camera 40.1 of the electronic imaging unit 40 is connected to a distal end of a cable (not shown). The cable, e.g. a ribbon cable, extends through the bore 36 and into the handle portion 12 of the otoscope 10. A distal end of the cable is connected to a logic unit 44, such as a microprocessor, which is schematically illustrated in FIG. 1. Similarly, the light guides 42 (not shown in FIG. 1) extend through the bore 36 and into the handle portion 12 of the otoscope 10. Proximal ends of the light guides 42 are connected to four LEDs 46, respectively. The LEDs 46 are positioned—like the logic unit 44—within the handle portion 12 of the otoscope 10. The LEDs 46 can be individually switched on and off. Furthermore, the handle portion 12 preferably comprises a memory 48 for storing images captured by the electronic imaging unit 40 or camera 40.1. The memory may be formed e.g. by a storage card slot and a corresponding storage card inserted in the slot. The handle portion 12 may further comprise a display (not shown) for displaying the images taken by the electronic imaging unit 40 or camera 40.1 to the user. Additionally or alternatively, the handle portion 12 may comprise a cable connection port, such as an USB-port, and/or a wireless connection, such as Bluetooth®, WIFI® and/or an energy supply, such as a (rechargeable) battery. These additional (optional) components of the handle portion 12 are known e.g. from digital cameras.

For capturing images of a patient's inner part of the outer ear canal, and in particular of a patient's eardrum, the distal end 18 of the head portion 14 has to be introduced into the patient's ear canal. Due to the shape of the head portion 14 there is no risk to insert the distal end 18 too deeply into the ear canal. That is, the shape and geometry of the distal end 18 does not allow significantly introducing the distal end point 34 into the patient's inner part of the outer ear canal which is pain sensitive. Therefore, injuries to the skin of the inner part of the outer ear canal and/or the eardrum can be reliably avoided. The geometry and the technology of the inventive otoscope do not require deforming the patient's ear as with a classic otoscope, as described above. Consequently, the otoscope according to the present invention can also be securely applied by laypersons.

Even though the distal end 18 of the head portion 14 will not be inserted into the inner part of the outer ear canal, the otoscope according to the present invention, nevertheless, allows for capturing images from the inner part of the outer ear canal and the eardrum, because of the electronic imaging unit 40 comprising a wide angle camera being provided at the distal end 18 of the head portion 14. In order to improve the ability of the electronic imaging unit 40 to "see" the eardrum, the camera of the electronic imaging unit 40 is placed offset from the longitudinal axis A of the head portion 14. Furthermore, the main "viewing direction" of the camera of the electronic imaging unit 40, corresponding to the bore axis B, is angled or tilted with respect to the longitudinal axis A of the head portion 14. The bore axis B and the longitudinal axis A intersect at a point having a predetermined distance from the distal end point 34, wherein the predetermined distance corresponds to the typical length of a patient's inner part of the outer ear canal, so that the camera of the electronic imaging unit 40 is directed to the eardrum.

When the distal end 18 of the head portion is introduced in the patient's ear canal, it may happen that artifacts, such as earwax particles or hair, in front of the electronic imaging unit 40, e.g. adhering to the probe cover, partially or even fully obstruct the view onto to eardrum. Therefore, the motion mechanism 24 may turn the rotatable portion 20 of the head portion 14 with respect to the remaining otoscope 10 about its axis of rotation R. For example, the motion mechanism 24 may rotate the rotatable portion 20 from an initial position by about 120° in clockwise direction, then from the initial position by about 120 in counter-clockwise direction, and finally return to the initial position. The camera 40.1 may capture one or more images from each of these equally spaced three positions. The logic unit 44 may identify different objects in the patient's ear by comparing the images received from the camera 40.1. In particular, the logic unit 44 may discriminate artifacts from the eardrum by determining their distance to the camera 40.1 according to the principle of stereoscopic viewing, as described in more detail above.

In order to further improve the identification process more than one image may preferably be taken from each of the three positions of the camera 40.1, with different LEDs 46 switched on and off for each captured image. Illumination of the artifacts and the eardrum from different positions also assists to discriminate these objects, as described in more detail above.

Finally, a new image may be generated (preferably by the logic unit 44) in which the identified artifacts are eliminated, so as to clearly show the eardrum. The degree of reddishness of the eardrum can then be easily determined. The user may be provided with corresponding information, such as to see the physician because of the risk of otitis media, or not. Also if the otoscope failed to detect the eardrum because of massive earwax in the patient's ear canal, corresponding information may be provided to the user. The user may then decide to visit a physician for having his or her ear canal cleaned.

Figure 5:
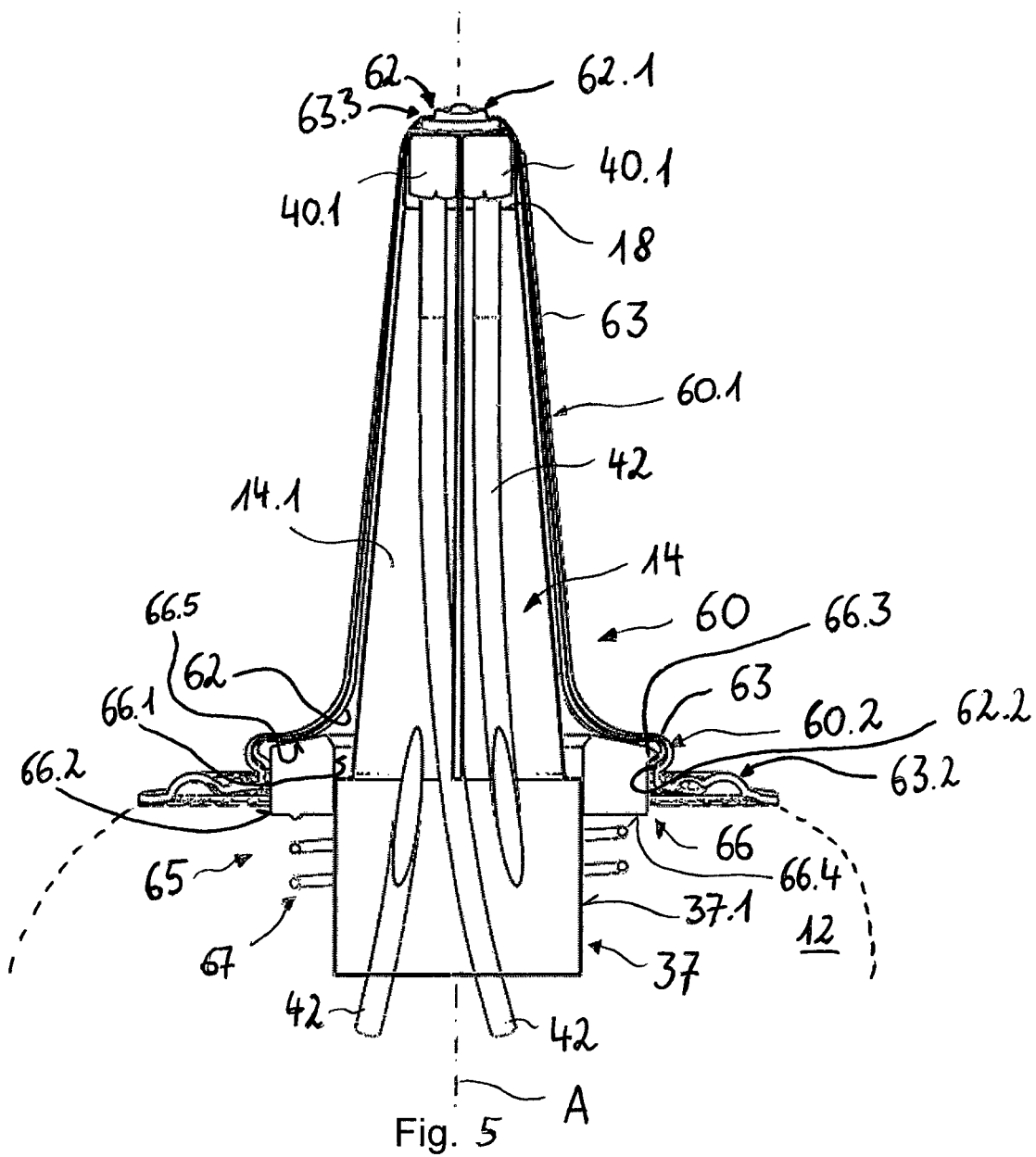
FIG. 5 schematically shows a cross-sectional view of a head portion of a further embodiment of an otoscope according to the present invention, the otoscope comprising a double-ply probe cover which is positioned in a first position.

FIG. 5 shows a head portion 14 of an otoscope, the head portion 14 being connected to a handle portion 12. The head portion 14 exhibits a distal end 18, a conical portion 14.1 and a proximal portion 37. The proximal portion 37 has a cylindrical shape. Within the head portion 14, at least three light guides 42 and cameras 40.1 are arranged. The cameras 40.1 are positioned at the distal end 18 with a radial offset with respect to a longitudinal axis A of the head portion 14. The head portion 14 is covered by a probe cover 60. The probe cover 60 exhibits an inner shell 62 and an outer shell 63. The probe cover 60 is a double-ply probe cover 60, i.e. a double sleeve probe cover. Both shells 62, 63 can be made of a similar material. The shells 62, 63 exhibit a similar shape, which at least partially corresponds to the shape of the head portion 14. In particular, at a distal tip, the inner shell 62 exhibits a distal portion in the form of a compressed or folded portion 62.1 which provides supplemental material of the inner shell 62 at the distal tip. The folded portion 62.1 provides a probe cover reserve. Preferably, the portion 62.1 exhibits concentric circular bends or plaits or folds, in particular a number between 2 and 10, preferably 3 and 8, more preferable 4 and 6, especially 5 bends or folds. It has been found that such a number can ensure an effective unfolding mechanism, wherein the folded portion does not require much space. A probe cover reservoir in the form of concentric circular bends or folds provides the advantage that any groove within the distal end of the head portion for accommodating the probe cover reservoir is not necessarily required. In contrast, the shape of the distal front side of the head portion can be even or plain. This enables accommodating a further sensor, e.g. an infrared sensor, centrically at the distal tip.

Figure 7:
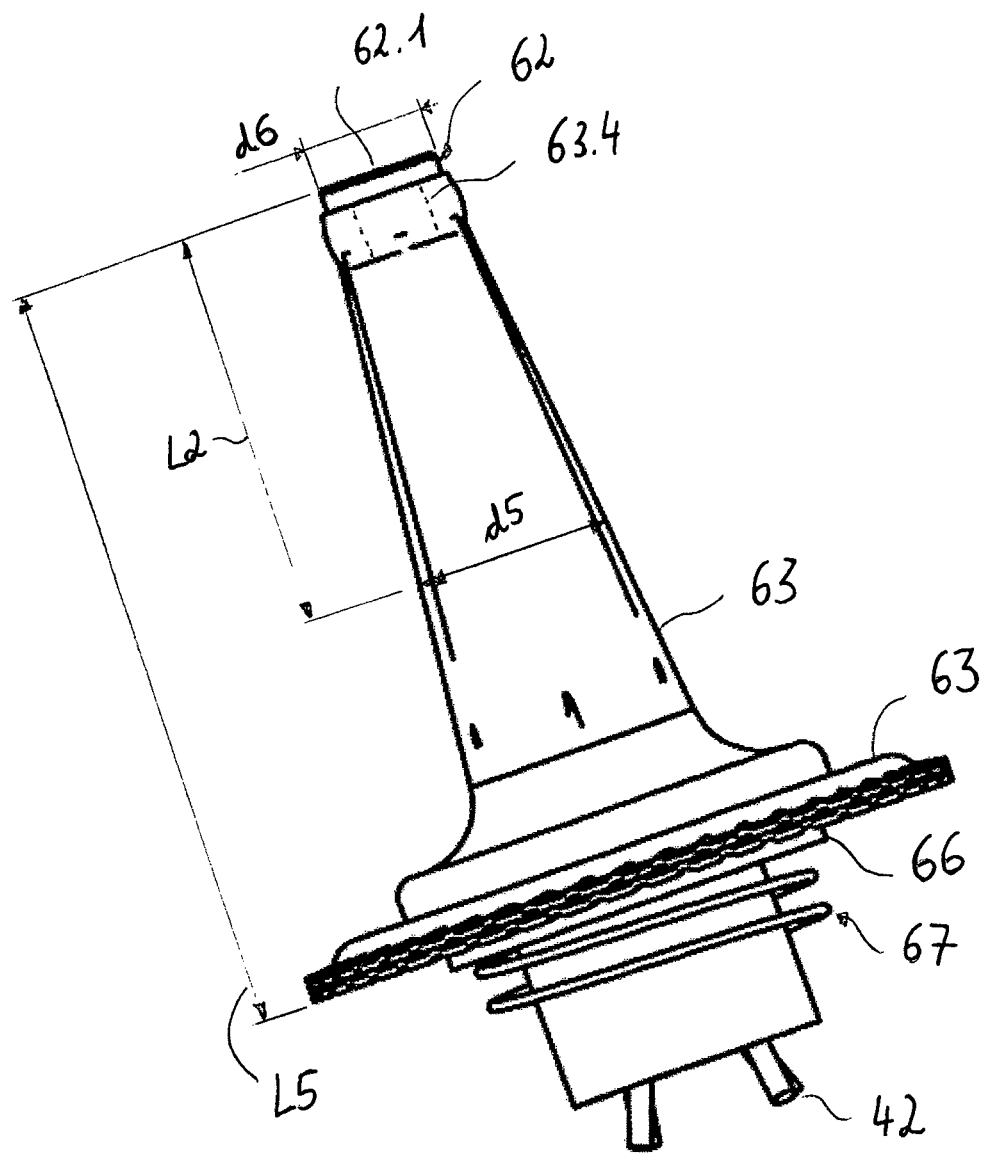
FIG. 7 schematically shows a side view of the head portion and the probe cover shown in FIG. 6.

At a distal tip, the outer shell 63 exhibits an aperture or opening 63.3. Additionally or as an alternative, at a distal tip, the outer shell 63 can exhibits a predetermined breaking or unfolding point or section 63.4 (as shown in FIG. 7), e.g. a perforation or an incision or an indentation or a notch. In particular, the opening 63.3 can exhibit a circular shape and can have a diameter which is slightly smaller than the diameter of the distal tip of the head portion. Preferably, the diameter of the opening 63.3 is slightly smaller than the diameter of the distal tip by a factor of ⅔ or ½, such that the outer shell 63 is elastically widened or dilated in a radial direction when the probe cover is axially moved with respect to the head portion 14. An opening 63.3 which is smaller than the diameter of the distal tip can ensure that ear wax or any other objects of a patient can be displaced towards the lateral surface of the head portion 14 more effectively.

Preferably, the wall thickness of the probe cover 60 is in a range between 0.05 mm and 0.15 mm, more preferable between 0.07 mm and 0.13 mm, especially about 0.1 mm. The inner shell 62 and the outer shell 63 may exhibit the same wall thickness, at least approximately. As both the inner shell 62 and the outer shell 63 can be produced by deep-drawing, in a distal direction, the wall thickness of both the inner shell 62 and the outer shell 63 may decrease towards the distal end. Preferably, the wall thickness of the folded portion 62.1 is in a range between 0.01 mm and 0.05 mm, more preferable between 0.02 mm and 0.04 mm, especially about 0.02 mm. It has been found that such a wall thickness does not affect the visibility, especially in case the inner shell 62 is made of polypropylene (PP). Preferably, the wall thickness of a conical portion of the inner shell 62 as well as the wall thickness of a conical portion of the outer shell 63 is in a range between 0.02 mm and 0.5 mm, more preferable between 0.02 mm and 0.4 mm, further preferable between 0.02 mm and 0.3 mm.

Preferably, both the inner shell 62 and the outer shell 63 are provided as disposable parts, such that the whole probe cover 60 is a disposable.

Also, it has been found that a relatively low thickness can be realized for each of the shells of the double-ply probe cover 60. Thereby, on the one hand, it is possible to deep-draw each of the shells. On the other hand, the probe cover 60 can be provided with a relatively high stiffness or dimensional stability, as both shells are in close contact with each other and can stabilize each other. Only at the distal tip, there is only one single shell, namely the inner shell, as (according to one alternative) the outer shell exhibits an opening at the distal tip.

Preferably, the inner shell 62 is made of an optically transparent material. The outer shell is not necessarily required to be made of an optically transparent material, as the outer shell exhibits an opening at the distal tip.

Further, the probe cover 60 exhibits a conical portion 60.1 and a groove, rim or undercut 60.2. In particular, this groove 60.2 can be provided by a section of the probe cover 60 which has a sigmoid shape. Preferably, at a proximal end, the inner shell 62 exhibits an U-shaped edge 62.2, and the outer shell 63 exhibits a sigmoid shaped section 63.1 and a radially protruding discoid collar 63.2 (as shown). The collar 63.2 overlaps the handle portion 12 in a radial direction. The collar 63.2 is arranged to partially cover the handle portion 12, especially a cavity in which a probe cover moving mechanism 65 is accommodated, and to protect the handle portion 12 and the moving mechanism 65, e.g. from any body fluids of a patient.

The collar 63.2 is arranged to be fixed at the handle portion 12 and/or at a stationary portion of the head portion 14. Preferably, the collar 63.2 is fixed at the handle portion 12 such that the collar 62.3 is arranged to transmit a torque from the probe cover 60 to the handle portion 12, in order to prevent rotation of the probe cover 60. In other words: Fixing the collar 63.2 at the handle portion 12 can ensure that the probe cover 60 does not rotate with respect an ear canal when the head portion 14 is rotated within the ear canal, be it manually or by means of a moving mechanism (not shown). Reducing relative motion between the patient's tissue confining the ear canal and the probe cover 60 can prevent irritation of the patient's tissue. In case of rotation, keeping or positioning the probe cover non-moving within the ear canal is preferred. Fixation mechanism may snap in (e.g. by means of three protrusions) into an undercut of the probe cover, but the rotatable portion of the head portion may rotate relative to the snap in fixation.

Preferably, the probe cover 60 is made of polypropylene (PP), especially both the inner shell 62 and the outer shell 63, especially by a thermoforming process, e.g. by means of thin sheets (e.g. 0.38 mm). It has been found that both the inner shell 62 and the outer shell 63 can be produced by deep-drawing. Polypropylene (PP) also provides the advantage of relatively high stiffness. Thereby, it can be ensured that any portions of the probe cover 60 are not displaced until a specific threshold value of an axial force exerted on the probe cover 60 is exceeded. Polypropylene has an elastic modulus of 1.5 GPa-2 GPa, which is relatively stiff. In contrast, polyethylene is more elastic (0.11 GPa-0.45 GPa) and thus less stiff, same as rubber (0.01 GPa-0.1 GPa). As an alternative, the probe cover 60 can be made of polytetrafluoroethylene (PTFE) and can be provided with a porous, gas-permeable structure, at least partially, especially in sections which do not require optical transparency.

The otoscope includes a probe cover moving mechanism 65 which is at least partially arranged between the head portion 14 and the probe cover 60. The moving mechanism 65 includes an adapter 66 and a moving device 67. Preferably, the adapter 66 is connected to the moving device 67 and hold by the moving device 67 in an axial position. Preferably, the adapter 66 is a ring-shaped element exhibiting an inner lateral surface 66.1 and an outer lateral surface 66.2. Preferably, the inner lateral surface 66.1 and the outer lateral surface 66.2 are arranged in parallel to each other. Preferably, the inner lateral surface 66.1 has the same shape as an outer lateral surface 37.1 of the proximal portion 37. In particular, the inner lateral surface 66.1 is arranged to contact the outer lateral surface 37.1 and to slide on the outer lateral surface 37.1. The adapter 66 further exhibits fixing means 66.3, e.g. a kind of collar or radial protrusion or radially protruding edge or rim 66.3, which engages the rim 60.2. In other words: The fixing means 66.3 has a diameter which is bigger than the diameter of the corresponding section of the probe cover 60. Alternatively or in addition, the adapter 66 and/or the probe cover 60 may exhibit a thread for fixing the probe cover 60 at the adapter 66.

The adapter 66 further exhibits a proximal surface, especially a proximal front surface 66.4, which is arranged for transmitting a force in a direction which is at least approximately parallel with the longitudinal axis A. Preferably, the adapter 66 is connected to the moving device 67 and hold by the moving device 67 in an axial position. The adapter 66 further exhibits a distal surface, especially a distal front surface 66.5, which is arranged for transmitting a force in a direction which is at least approximately parallel with the longitudinal axis A. The distal front surface 66.5 is orientated at an angle with respect to the longitudinal axis A which is smaller or bigger than 90°. The distal front surface 66.5 is orientated at an angle with respect to the proximal front surface 66.4 which is preferably in a range between 10° and 50°, more preferable 15° and 30°. The distal front surface 66.5 provides a contact surface for the probe cover 60, especially the inner shell 62. The distal front surface 66.5 corresponds with the probe cover 60, especially with the inner shell 62.

In particular, the moving device 67 can comprise an energy storage, especially in the form of an elastic element. The elastic element preferably is made of metal. The moving device 67 can allow for a mechanical retraction. Preferably, the moving device 67 allows for an axial displacement of about 2 mm. The moving device 67 acts on the front surface 66.4, especially in a direction which is parallel with the longitudinal axis A. For example, the moving device 67 comprises an elastic spring, especially a cylindrical compression spring (as shown), or any alternative elastic element providing the same effect. The moving device 67 shown in FIG. 5 is a mechanical moving device. Optionally, the moving device 67 can be provided as an electric component, e.g. a motor, especially a linear motor. Also, the moving device 67 can be provided as a latch mechanism. In particular, the latch mechanism can exhibit two predefined positions, a first position in which the distal portion (i.e. the probe cover reservoir) of the inner shell is folded, and a first position in which the distal portion of the inner shell is unfolded. These two positions can be defined, e.g., by limit stops or locking devices. The latch mechanism can be coupled to the imaging unit and/or a logic unit. The latch mechanism can be released or actuated manually or automatically. In particular, the latch mechanism can be released in dependence on a signal emitted from the electronic imaging unit, especially a signal which is emitted when (as soon as) the electronic imaging unit is in visual communication with the eardrum. The latch mechanism may comprise an electromagnetic latch which allows to unblock the axial movement upon an electrical signal.

Preferably, in the position shown in FIG. 5, the moving device 67 is not prestressed or elastically preloaded, i.e. the moving device 67 is discharged or relieve of any load. Optionally, the moving device 67 can be preloaded, i.e., the moving device 67 can be supported with a pretension exerted on the probe cover 60. Referring to the position shown in FIG. 5, in case the moving device 67 is arranged for being elastically preloaded, the head portion 14, especially the proximal portion 37, can exhibit a protrusion or a limit stop or locking device (not shown) which ensures that the adapter 66 is not pushed further in the distal direction, but remains in an axial position in which the probe cover 60 can be supported in the first position (as shown) by the adapter 66. Such a pretension can define a threshold value for an axial force which has to be exerted on the adapter 66 in the proximal direction, in order to axially move the probe cover 60 in the proximal direction. Preferably, the moving device 67 is supported by an appropriate supporting structure (not shown) of the head portion 14 or the handle portion 12.

In the following, referring to FIGS. 5 and 6, the functioning of the moving mechanism 65 is explained, especially in conjunction with the double-ply probe cover 60.

First, the probe cover 60 is mounted on the head portion 14, especially in such a way that an inner surface of the probe cover 60 gets in contact with the adapter 66, especially the distal front surface 66.5. Then, the head portion 14 is introduced into the ear canal. As soon as the probe cover 60 gets in contact with an inner lateral surface of the ear canal, a friction force is exerted on the probe cover 60. The friction force depends on the position of the head portion 14 within the ear canal: the friction force increases with increasing insertion depth. The frictional force is directed backwards, i.e. in the direction of the handle portion 12. As the probe cover 60 is in contact with the adapter 66, the frictional force is transmitted to the adapter 66 and to the moving device 67 in the axial direction, at least partially.

As the adapter 66 is axially displaceable or movable, the probe cover 60 can be moved axially with respect to the head portion 14. The compressed or folded portion 62.1 can be unfolded by axial motion of the probe cover 60 with respect to the head portion 14. In other words: The folded portion 62.1 can be unfolded such that only the portion 62.1 (in an unfolded state) of the inner shell 62 covers the distal tip of the head portion 14. The outer shell 63 does not cover the distal tip.

Figure 6:
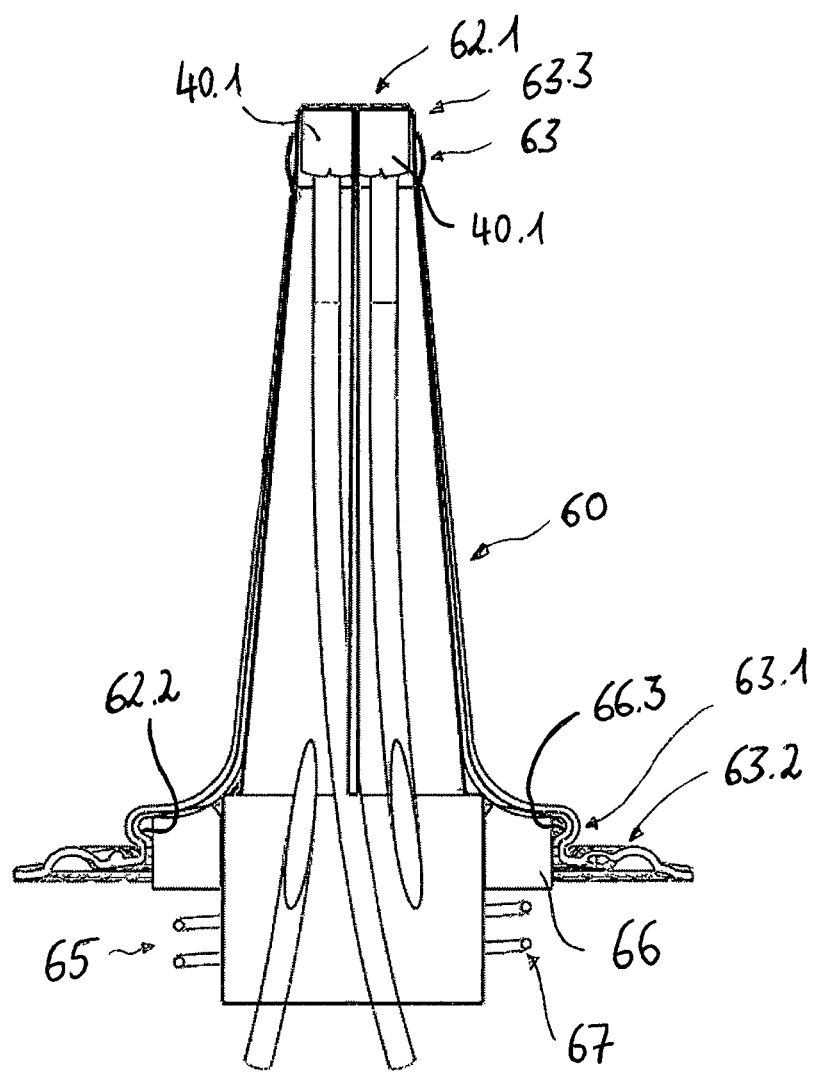
FIG. 6 shows the head portion and the probe cover shown in FIG. 5, the probe cover being positioned in a second position.

FIG. 6 shows the probe cover 60 and the adapter 66 in a second axial position in which the spring 67 is elastically preloaded, i.e. at least partially compressed in the proximal direction. The portion 62.1 of the inner shell 62 closely fits the distal tip of the head portion 14. The portion 62.1 of the inner shell 62 is unfolded and fully in contact with the distal tip. The portion 62.1 covers the distal front side of the head portion and completely lies flat on the distal front side or the distal tip.

In the second position shown in FIG. 6, the cameras 40.1 are not covered by any object other than the inner shell 63. By means of the moving mechanism, the inner shell 63 can be stretched or tensioned. This method step of deploying or unfolding the probe cover 60 can ensure that a field of vision is free of any objects. Any ear wax or any other objects have been pulled away from the distal tip by means of the outer shell 63.

The head portion 14, especially the proximal portion 37, can exhibit a radial protrusion or a limit stop or locking device (not shown) which ensures that the adapter 66 is not pushed further in the proximal direction, but remains in an axial position in which the inner shell 62 is pulled or stretched onto the head portion 14 with a predefined tension. Such a locking device can ensure that the portion 62.1 is not tensioned or stretched more than a predefined threshold value.

As can be seen in FIG. 6, it is not required to provide any groove for accommodating the portion 62.1 of the inner shell 62 at the distal tip of the head portion 14. Nonetheless, the head portion 14 can exhibit a groove or recess arranged for accommodating the portion 62.1 or any other probe cover reserve.

Preferably, the moving mechanism 65 is electrically coupled with at least one of the cameras 40.1 and/or a logic unit. The moving mechanism 65 can exhibit a motion detector (not shown) which is arranged for detecting relative (axial) motion of the probe cover 60 with respect to the head portion 14. In case the probe cover 60 is axially displaced, the motion detector can emit an electric signal which is transmitted to the at least one camera 40.1 or any logical unit or control unit, evoking start-up or powering of the camera 40.1. In such a way, by means of motion detection or detection of the axial position of the probe cover 60, the camera 40.1 can be powered at a time when the camera 40.1 is in visual communication with the eardrum. Thereby, it is possible to reduce an amount of data which has to be processed. Also, the amount of energy required for observing the eardrum can be reduced. Additionally or as an alternative, the moving mechanism 65 can be actuated in dependence on a signal emitted from the camera 40.1, especially a signal which is emitted when (as soon as) the camera 40.1 is in visual communication with the eardrum.

Optionally, the electric signal can be transmitted to one or several light sources (not shown), in order to evoke start-up or powering of the light sources only when the camera 40.1 is in visual communication with the eardrum. Thereby, it is possible to reduce an amount of heat which is emitted by the light sources. Also, the amount of energy required for observing the eardrum can be reduced more effectively.

With the double-ply probe cover 60 shown in FIG. 6, gas (e.g. air) can be passed through one or several cavities arranged between the inner shell 62 and the outer shell 63. This allows for pressurizing the eardrum without any risk of contamination. In particular, the inner shell 62 fully covering the head portion can ensure that any contamination risk is minimized. The gas can be transferred to the distal tip of the probe cover 60. As the outer shell 63 does not (entirely) cover the distal tip, the gas can escape from the cavities and can be passed into the ear canal. There is no need for any porous, gas-permeable section.

FIG. 7 shows the probe cover 60 in the second axial position with respect to the head portion 14. Only the inner shell 62 is covering the distal tip of the head portion 14. Optionally, the distal end of the outer shell 63 can exhibit axial indentations or notches 63.4, as indicated by the dashed lines. The indentations or notches 63.4 can facilitate moving the distal end of the outer shell 63 from to distal front side of the head portion 14 to the lateral surface of the head portion 14. The total length L5 of the probe cover is in the range of 22 mm and 30 mm, preferably 24 mm and 28 mm, more preferable 25 mm and 27 mm, especially about 26 mm.

Figure 8:
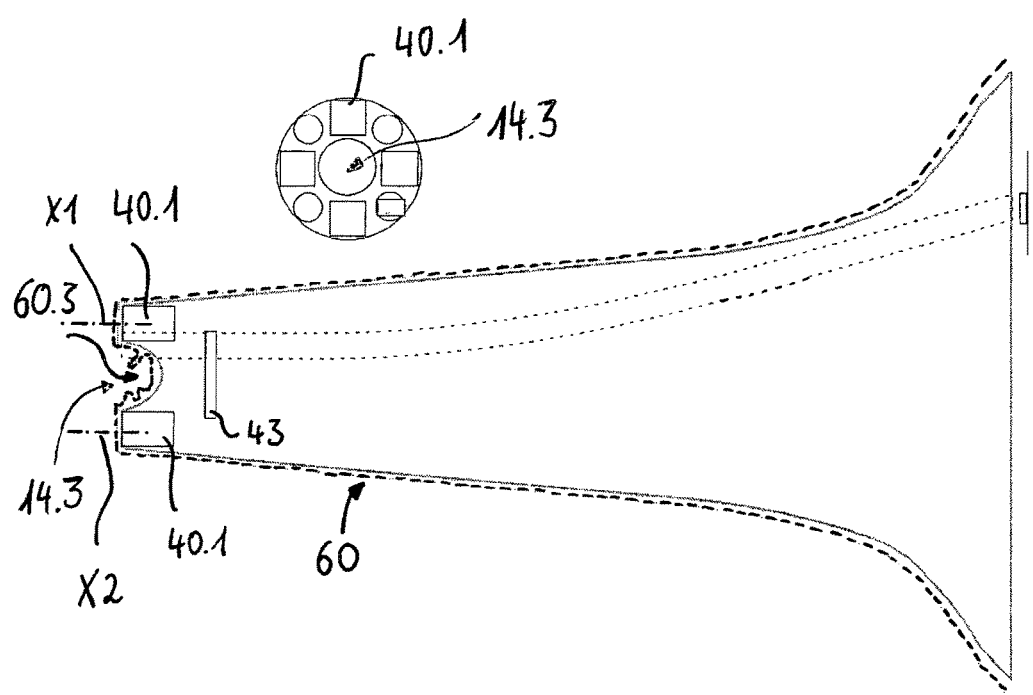
FIG. 8 schematically shows a cross-sectional view as well as a front side of a head portion of a further embodiment of an otoscope according to the present invention, the otoscope comprising a single-ply probe cover which is positioned in a first position.

At the distal tip, the probe cover 60 has an outer diameter d6 in the range of 4.1 mm to 6.1 mm, preferably 4.6 mm to 5.4 mm, further preferred 4.8 mm to 5.1 mm, especially 5 mm. In a central section of the widening (conical) portion, the probe cover 60 has an outer diameter d5, especially at an axial position defined by a specific length L2 which is preferably in the range of 28 mm to 32 mm, especially 20 mm. The diameter d5 is in the range of 7.6 mm to 9.6 mm, preferably 8.1 mm to 9.1 mm, further preferred 8.4 mm to 8.9 mm especially 8.9 mm FIG. 8 shows a further embodiment of a probe cover 60 which can be provided in conjunction with a moving mechanism (not shown), e.g. a moving mechanism as described in FIGS. 5 and 6. The probe cover 60 is a single-ply probe cover.

Preferably, the probe cover 60 is made of (at least partially) an hydrophobic porous material (e.g. porous polytetrafluoroethylene/PTFE) and can be provided with a porous, gas-permeable structure, at least partially. As an alternative, the probe cover 60 can be made of polypropylene (PP), especially by a thermoforming process.

The probe cover 60 is shown in a first axial position in which it has not been pulled or stretched onto the distal tip of the head portion 14 yet. A groove 14.3 is provided at the distal tip of the head portion 14. In the first position, a folded portion 60.3 of the probe cover 60 is arranged within the groove 14.3. The folded portion 60.3 provides a probe cover reserve. Cameras 40.1, especially four cameras, are provided adjacent to and/or around the groove 14.3. Each camera 40.1 exhibits or defines one optical axis X1, X2 which is positioned radially offset. Alternatively or in addition, beam splitter optics can be provided, wherein the beam splitter optics exhibit a plurality of eccentric optical axes which may share one centrally arranged image sensor 43.

When introducing the head portion 14 into the ear canal, ear wax or any other objects may adhere onto the probe cover 60, especially on a lateral surface of the probe cover 60. It has been found that it is not likely that ear wax or any other objects adheres on the folded portion 60.3, especially as the folded portion 60.3 is arranged centrically. While introducing the head portion 14, or after having introduced the head portion 14, the probe cover 60 can be pulled in the proximal direction, in order to pull any ear wax or any other objects away from the distal tip. Thereby, the folded portion 60.3 is stretched or tensioned, and a field of vision can be uncovered from any objects.

With the single-ply probe cover 60 shown in FIG. 8, in case the probe cover 60 exhibits at least one porous, gas-permeable section, gas (e.g. air) can be passed through the shell of the probe cover 60. This allows for, e.g., pressurizing the eardrum.

In the FIGS. 5, 6, 7 and 8, the probe cover 60 is shown as a cover having a wall thickness which is negligibly thin with respect to the radial dimensions of the head portion. The wall thickness may be constant, at least approximately, or may be tapered in a distal direction, at least in sections. Optionally, the probe cover 60 can provide a specific outer shape or geometry, especially a conical shape, at least partially. The conical shape can provide a specific conical shape of the head portion, e.g. a conical shape which is adapted for specific groups of persons, e.g. children, or female persons at the age of 30 to 50.

In the FIGS. 5, 6 and 7, a double-ply probe cover 60 is shown which exhibits an outer shell 63 which is in contact with the inner shell 62, especially at every section of the outside circumference. As an alternative, a double-ply probe cover exhibiting an inner shell with fins, or with lands which provide gap openings or slots or longitudinal grooves there between can be provided. The fins or lands can protrude in a radial direction. Preferably, the fins or lands are orientated in a direction which is parallel to the longitudinal axis of the head portion, at least approximately. Such a configuration can evoke capillary forces within gap openings or slots between the inner and outer shell. The outer shell can be in contact with the fins or lands of the inner shell, and in case of capillary forces also with an outer lateral surface of the inner shell in a section between the fins or lands. The capillary forces may prevent any fluid passing through the probe cover. Thus, a probe cover which allows for both pressurizing the ear canal and reduced risk of infections can be provided. An inner shell with fins or lands which provide gap openings or slots or longitudinal grooves there between can be produced e.g. by deep-drawing.

FIG. 9A shows a double-ply probe cover 60 which is arranged in a first position on a head portion 14 of an otoscope, the head portion 14 exhibiting a conical shape. The probe cover 60 exhibits an inner sleeve or shell 62 and an outer sleeve or shell 63. At a distal portion, the inner shell 62 exhibits a probe cover reservoir 62.1, provided in the form of a folded film or foil portion. The reservoir 62.1 exhibits concentric circular bends or plaits or folds. Other shapes of the folded portion may be desirable in order to facilitate thermoforming of the part. At a distal portion, the outer shell 63 exhibits an opening 63.3. The diameter of the opening 63.3 is smaller than the diameter of the distal tip of the head portion 14. In particular, the diameter of the opening 63.3 is in a range between half of the diameter of the distal tip and ⅓ of the diameter of the distal tip.

In FIG. 9B, the double-ply probe cover 60 shown in FIG. 9A is arranged in a second position, especially within an ear canal (not shown). With respect to FIG. 9A, both the inner shell 62 and the outer shell 63 have been displaced in a proximal direction, especially by a pulling force, as indicated by the two arrow heads. The probe cover reservoir 62.1 has been unfolded by the displacement. The diameter of the opening 63.3 at least approximately corresponds to the diameter of the distal tip of the head portion 14. At the distal tip, the outer shell 63 has been deformed, be it elastically or plastically. The opening 63.3 frames or limits or bounds the distal tip of the head portion 14. In the second position, the reservoir 62.1 does not exhibit concentric circular bends or plaits or folds any more. In contrast, the reservoir 62.1 is stretched or tensioned.

FIG. 9C shows a single-ply probe cover 60 which is arranged in a first position on a head portion 14 of an otoscope, the head portion 14 exhibiting a conical shape. At a distal portion, the probe cover 60 exhibits a probe cover reservoir 60.3, provided in the form of a folded film or foil portion, in particular a single-ply or single-layer folding or bending. The reservoir 60.3 is provided by a portion of the probe cover which annularly overlaps an outer section of a distal tip of the probe cover. Preferably, the overlap is in the range of 30% to 100% with respect to the radial dimensions of the distal tip, further preferred the range of 50% to 90%, most preferred the range of 60% to 80%. In a folded status, the profile of the distal portion of the probe cover 60 exhibits a sigmoid shape. At the distal portion, in the folded status, the probe cover 60 forms a three-ply section. The three-ply section can cover the whole distal tip of the head portion 14.

Figure 9F:
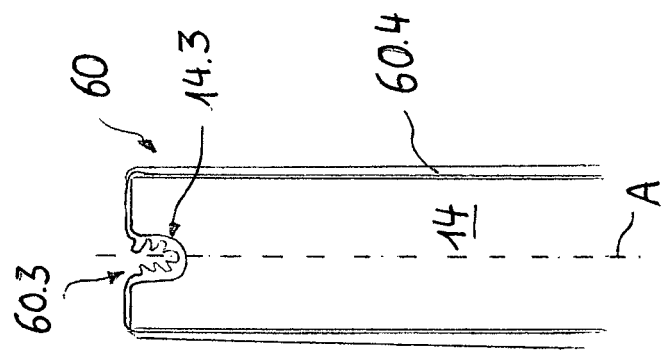
Figure 9E:
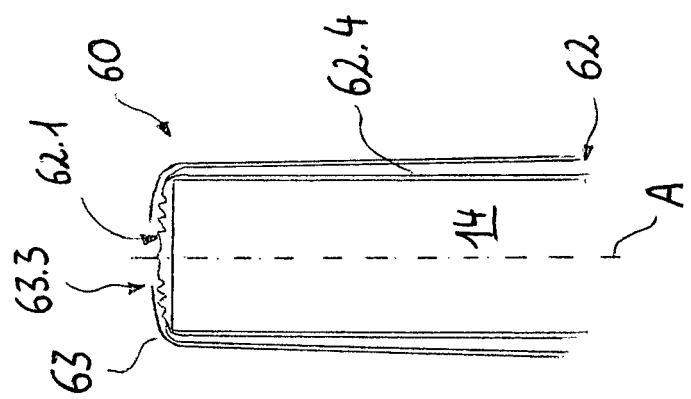
Figure 9D:
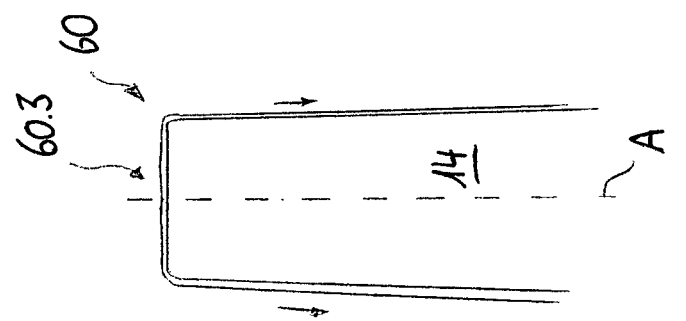

In FIG. 9D, the double-ply probe cover 60 shown in FIG. 9C is arranged in a second position, especially within an ear canal (not shown). With respect to FIG. 9C, the probe cover has been displaced in a proximal direction, especially by a pulling force, as indicated by the two arrow heads. The reservoir 60.3 has been unfolded. In the second position of the probe cover 60, the reservoir 60.3 is stretched or tensioned.

FIG. 9E shows a double-ply probe cover 60 which is arranged in a first position on a head portion 14 of an otoscope, the head portion 14 exhibiting a cylindrical shape. The probe cover 60 exhibits an inner sleeve or shell 62 and an outer sleeve or shell 63. At a distal portion, the inner shell 62 exhibits a probe cover reservoir 62.1, provided in the form of a folded portion. In a first position (as shown), the reservoir 62.1 exhibits concentric circular bends or plaits or folds. At a distal portion, the outer shell 63 exhibits an opening 63.3. By means of an axial movement in the proximal direction relative to the head portion 14, the reservoir 62.1 can be unfolded and stretched, and the opening 63.3 can be dilated.

The inner shell 62 exhibits a wall thickness diverging in the proximal direction. The inner shell 62 provides a conical shape. The inner shell 62 exhibits a conical portion 62.4 with a cylindrical inner lateral surface which corresponds with the outer cylindrical lateral surface of the head portion 14.

FIG. 9F shows a single-ply probe cover 60 which is arranged in a first position on a head portion 14 of an otoscope, the head portion 14 exhibiting a cylindrical shape. The probe cover 60 exhibits a reservoir 60.3 which is accommodated within a groove 14.3 at a distal tip of the head portion 14. The reservoir 60.3 is provided by a portion of the probe cover which is arranged centrally at a distal tip of the probe cover. By means of an axial movement in the proximal direction relative to the head portion 14, the reservoir 60.3 can be unfolded and stretched.

The probe cover 60 exhibits a wall thickness diverging in the proximal direction. The probe cover exhibits a conical portion 60.4 with a cylindrical inner lateral surface which corresponds with the outer cylindrical lateral surface of the head portion 14.

In the embodiments shown in FIGS. 9A to 9F, a small gap or mechanical play between the distal tip of the head portion 14 and the distal tip of the probe cover 60 can be provided, the gap preferably being in the range between 0.1 mm and 0.2 mm, especially 0.15 mm. This gap can facilitate displacement or unfolding of the probe cover 60.

Figure 10A:
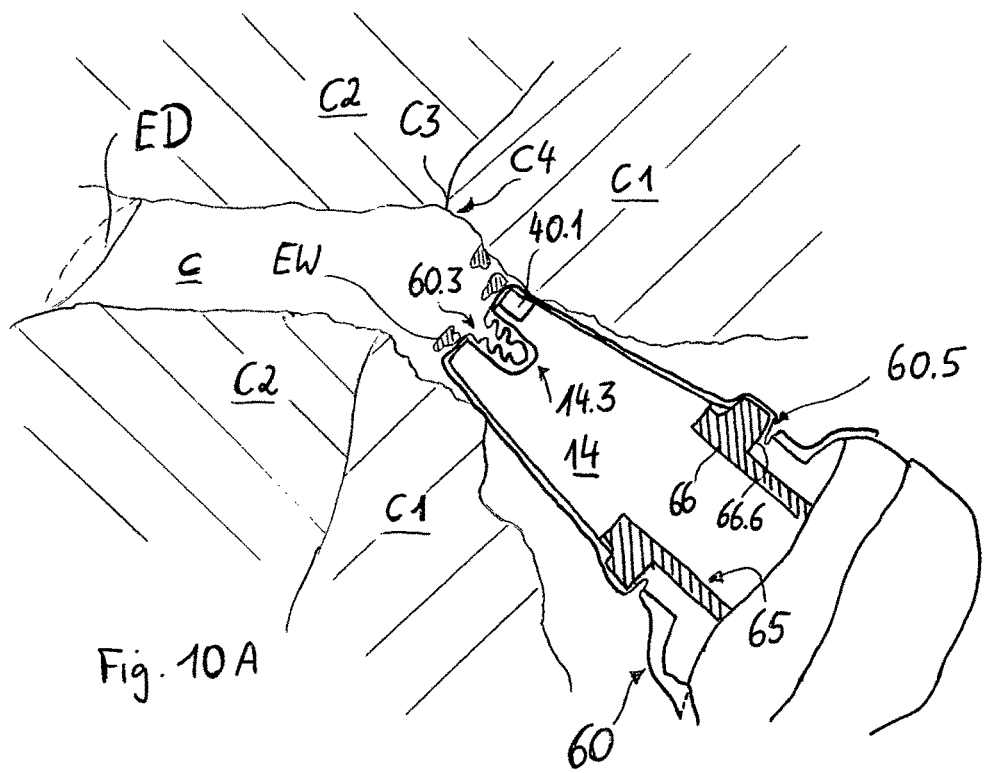
FIGS. 10A and 10B schematically show cross-sectional views of a probe cover arranged on a head portion of a further embodiment of an otoscope according to the present invention, the head portion being positioned in a first and second position within an ear canal.

FIG. 10A shows a head portion of an otoscope which is arranged within an ear canal C. The ear canal C is partly surrounded or confined by soft connective tissue C1 and—further down towards the eardrum ED—partly by hard bone C2. In order to appropriately observe the eardrum ED, the head portion 14 has to be introduced as far as a curvature C4 which is located at a transition point C3 between the soft connective tissue C1 and the hard bone C2. A camera 40.1 is arranged with a radial offset within the head portion 14.

Further, a moving mechanism 65 is arranged within the head portion 14. The moving mechanism 65 exhibits an adapter 66 having a shoulder 66.6. The adapter 66 is shown in a first position. A probe cover 60 exhibiting a probe cover reservoir 60.3 is provided over the head portion 14. The head portion 14 exhibits a groove or indentation 14.3 for accommodating the probe cover reservoir 60.3. The probe cover 60 exhibits a U-shaped or sigmoid shaped section or inward protrusion which engages or encompasses the shoulder 66.6 such that the probe cover 60 can be positioned axially by means of the moving mechanism 65. The axial position of the probe cover 60 can be defined by the moving mechanism 65, i.e. by the axial position of the adapter 66.

Ear wax EW and/or other objects are partially obstructing the ear canal C. In particular, ear wax EW adheres on the outer surface of the probe cover 60 and obstructs any optical line of sight or any visual communication of the camera 40.1 with the eardrum ED.

Figure 10B:
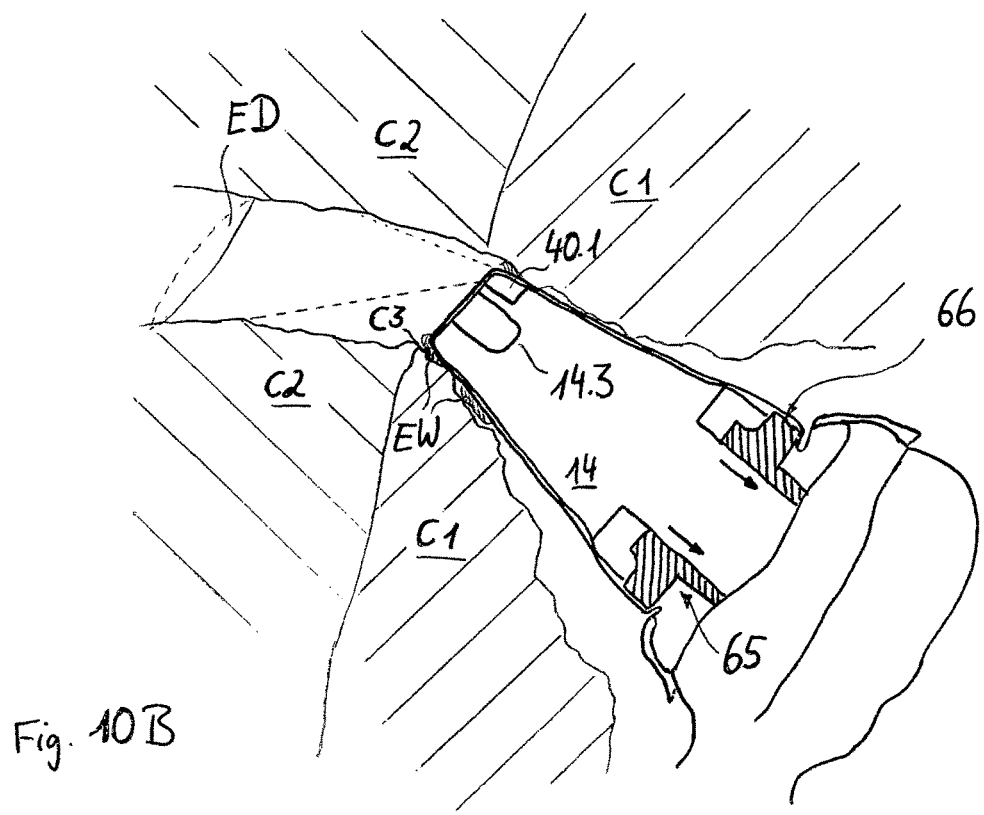

FIG. 10B shows the head portion 14 in a second position within the ear canal. The distal tip of the head portion 14 is introduced as far as the transition point C3. The probe cover 60 and the adapter 66 have been displaced in a proximal direction, as indicated by the two arrow heads. Thereby, a pulling force in the proximal direction is exerted on the probe cover 60. The adapter 66 is shown in a second axial position. The probe cover reservoir 60.3 has been pulled out of the indentation 14.3. The reservoir 60.3 has been displaced from the distal tip towards a lateral surface of the head portion 14, at least partially. Thereby, ear wax EW has been displaced towards the lateral surface, too. The field of vision of the camera 40.1 is not obstructed by any ear wax any more.

Figure 11A:
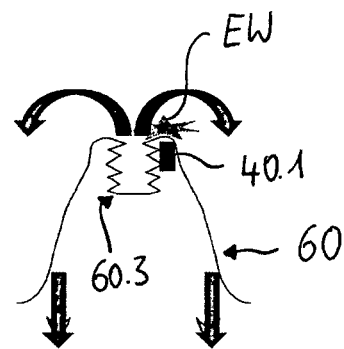
FIGS. 11A and 11B schematically show cross-sectional views of a probe cover which can be arranged on a head portion of an otoscope according to the present invention, the probe cover being shown in a first and second position.
Figure 11B:
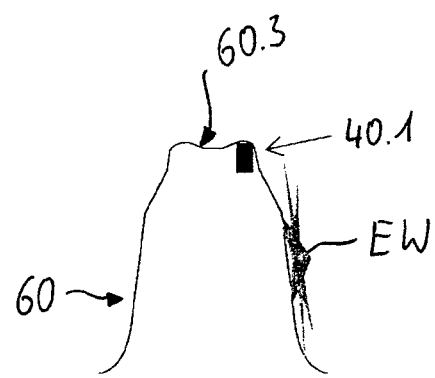

FIG. 11A schematically shows a probe cover 60 exhibiting a folded probe cover reservoir 60.3. The reservoir 60.3 can be displaced radially outwards and backwards in a proximal direction, as indicated by the arrow heads. In the position of the probe cover 60 as shown in FIG. 11A, ear wax EW obstructs the field of vision of a camera 40.1. FIG. 11B shows the probe cover 60 in an axially displaced position. The ear wax EW has been displaced towards a lateral surface of a head portion (not shown) on which the probe cover 60 is arranged.

The probe covers 60 shown in the previous figures may be used in conjunction with pressurizing means.

Figure 12A:
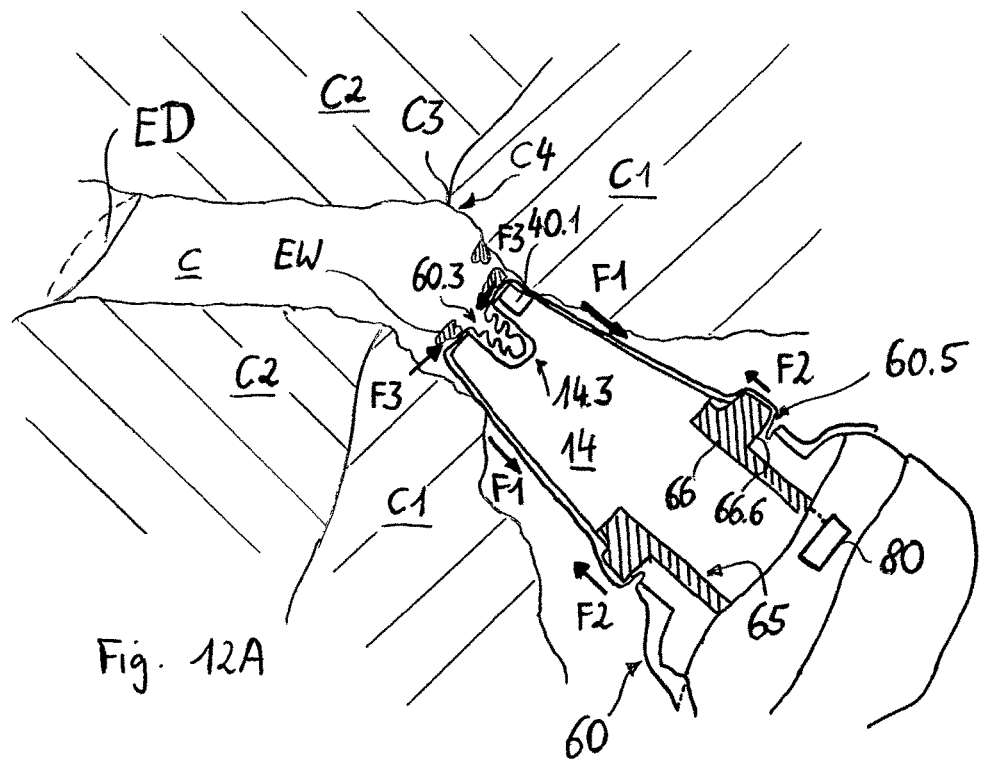
FIGS. 12A and 12B schematically show cross-sectional views of a probe cover arranged on a head portion of a further embodiment of an otoscope according to the present invention, the head portion being positioned in a first and second position within an ear canal.

FIG. 12A shows a head portion of an otoscope which is arranged within an ear canal C. The ear canal C is partly surrounded or confined by soft connective tissue C1 and—further down towards the eardrum ED—partly by hard bone C2. In order to appropriately observe the eardrum ED, the head portion 14 has to be introduced as far as a curvature C4 which is located at a transition point C3 between the soft connective tissue C1 and the hard bone C2. A camera 40.1 is arranged with a radial offset within the head portion 14.

Further, a moving mechanism 65 is arranged within the head portion 14. The moving mechanism 65 exhibits an adapter 66 having a shoulder 66.6. The adapter 66 is shown in a first position. A probe cover 60 exhibiting a probe cover reservoir 60.3 is provided over the head portion 14. The head portion 14 exhibits a groove or indentation or probe cavity 14.3 for accommodating the probe cover reservoir 60.3. The probe cover 60 exhibits a U-shaped or sigmoid shaped section or inward protrusion which engages or encompasses the shoulder 66.6 such that the probe cover 60 can be positioned axially by means of the moving mechanism 65. The axial position of the probe cover 60 can be defined by the moving mechanism 65, i.e. by the axial position of the adapter 66.

Ear wax EW and/or other objects are partially obstructing the ear canal C. In particular, ear wax EW adheres on the outer surface of the probe cover 60 and obstructs any optical line of sight or any visual communication of the camera 40.1 with the eardrum ED.

Figure 12B:
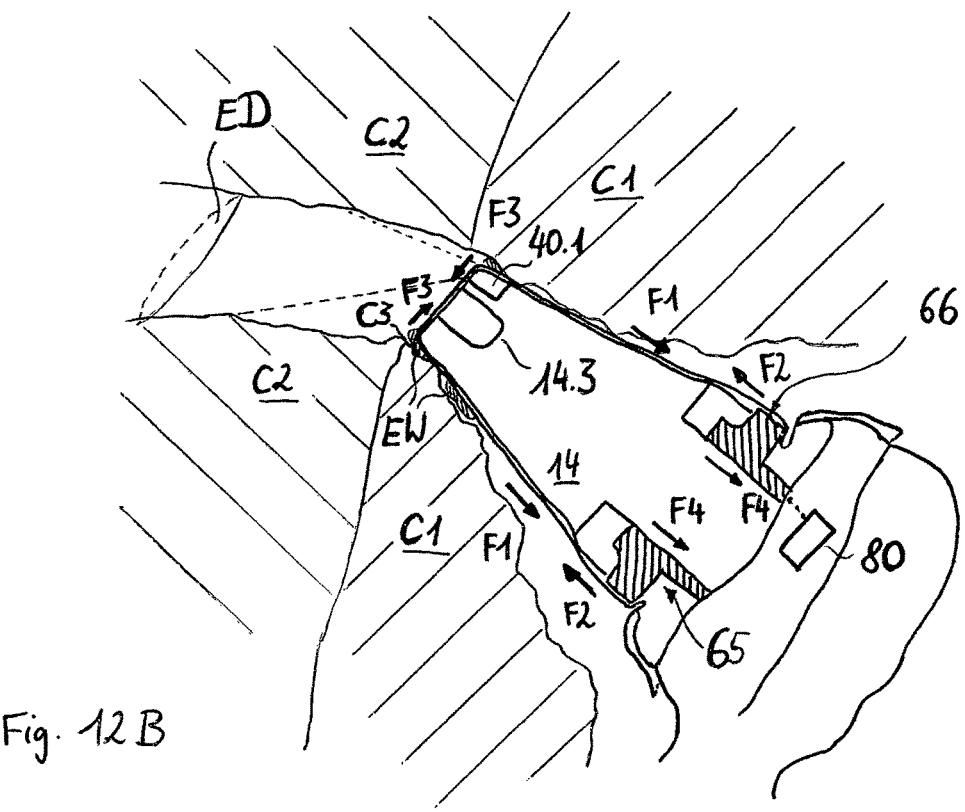

At the position within the ear canal C as shown in FIG. 12A, there are three main forces which are effective. There is a friction force F1 exerted between tissue, especially the soft connective tissue C1, and the outer lateral surface of the probe cover. A force F2, especially an introducing or insertion force, is exerted from the head portion 14 on the probe cover 60. A force F3 is exerted on the probe cover 60, the force F3 being a reaction force due to frictional forces which have to be overcome in order to unfold the probe cover reservoir 60.3. During insertion, i.e. prior to reaching a final position (as shown in FIG. 12B), the force F2 is bigger than the force F1, such that the head portion 14 can be introduced further. The force F3 is such that the frictional force F1 does not evoke unfolding. In order to provide a force F2 which is big enough for introducing the probe cover 60 in an unfolded state, the probe cover 60 is provided with an appropriate stiffness or rigidity, especially at the lateral surface section, but not at the distal tip.

FIG. 12B shows the head portion 14 in a second position within the ear canal. The distal tip of the head portion 14 is introduced as far as the transition point C3. The probe cover 60 and the adapter 66 have been displaced in a proximal direction, as indicated by the two arrow heads. Thereby, a pulling force F4 in the proximal direction has been exerted on the probe cover 60. The pulling force F4 is bigger than any reaction force F3 exerted by the probe cover 60. The pulling force F4 can be applied during insertion, i.e. in conjunction with the forces F1 and F2, or once the head portion 14 has been positioned in the end position within the ear canal C (when no forces F1, F2 are applied any more, as there is no relative motion between the head portion 14 and the ear canal C any more).

During the steps shown in FIGS. 12A and 12B, detection of a force exerted on the probe cover or the head portion can be carried out, especially by force detection means 80 which are coupled to the moving mechanism 65. The moving mechanism 65 can provide a reaction force (corresponding to the insertion force F2), especially in order to determine a threshold value for an axial force which has to be exceeded in order to axially displace the probe cover in the proximal direction with respect to the head portion. The force detection means 80 may be arranged for releasing the moving mechanism 65, especially at a time the threshold value is exceeded. Alternatively or in addition, the moving mechanism 65 may exhibit a latch mechanism which can be released upon a specific force. The force detection means 80 may exhibit a force sensor, e.g. any common force sensor arranged for detection a compression force.

Figure 13:
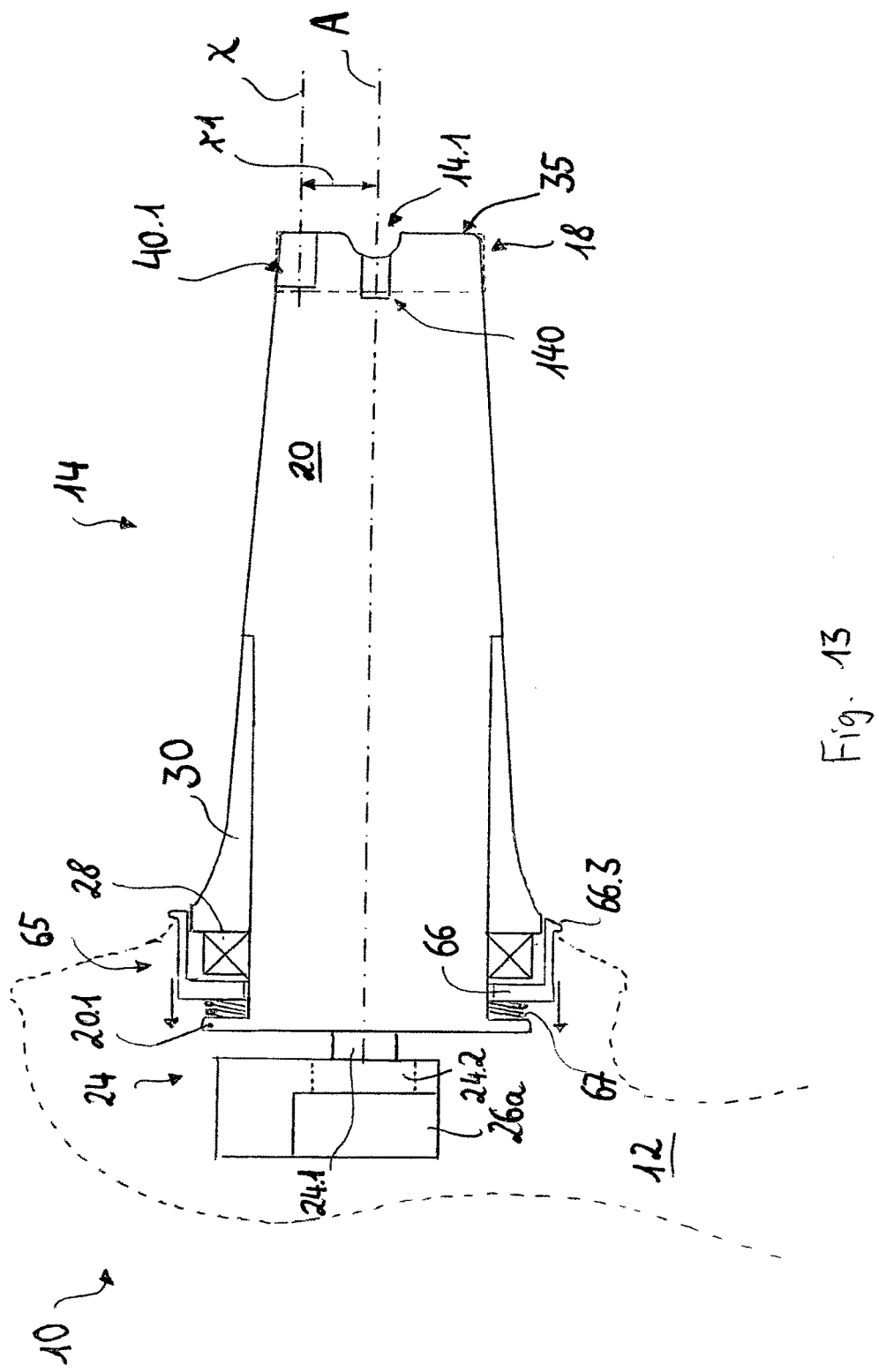
FIG. 13 schematically shows a cross-sectional view of a head portion and of a part of a handle portion of a further embodiment of an otoscope according to the present invention.

FIG. 13 shows an otoscope 10 with a handle portion 12 and a head portion 14. The head portion includes a movable portion 20 and a support structure 30. The movable portion 20 can be rotated by a motion mechanism 24 which is arranged in the handle portion 12. The movable portion 20 can be rotated with respect to the support structure 30. The motion mechanism 24 includes a drive shaft 24.1 which connects the movable portion 20 with the handle portion 12. The motion mechanism 24 includes a brushless motor 26a which is connected to the drive shaft 24.1. Optionally, a gear 24.2 is provided between the motor 26a and the drive shaft 24.1. The movable portion 20 is supported by the bearing 28 which is supported by the handle portion 12. The support structure 30 is supported by the handle portion 12. The support structure 30 provides a portion of the outer lateral surface of the head portion 14. The support structure 30 is fixed at the handle portion 12 by means of the bearing 28.

The head portion 14 has a distal end 18 including a distal tip 35, wherein the distal end 18 has conical shape or a cylindrical shape (as indicated by the dashed line). An infrared sensor unit 140 is positioned centrically at the distal end 18. This position is only illustrated as an example. The infrared sensor unit 140 shown in FIG. 13 can be provided in conjunction with the other embodiments of the otoscopes as described in the preceding or following figures also. The distal end 18 is provided with an indentation 14.3 for accommodating a portion of a probe cover (not shown). A camera 40.1 having an optical axis X is arranged radially offset with respect to a longitudinal axis A of the head portion 14, wherein the radial offset r1 of the optical axis X preferably is in a range between 1.5 mm and 2 mm. The camera 40.1 is arranged adjacent to an inner lateral surface of the distal end 18. Preferably, the camera 40.1 is in contact with the inner lateral surface of the distal end 18.

A probe cover (not shown) can be displaced by a moving mechanism 65, especially axially. Also, the axial position of the probe cover with respect to the head portion 14 can be defined by the moving mechanism 65. The moving mechanism 65 comprises an adapter 66 which exhibits at least one radial protrusion 66.3, especially a collar, which can be coupled with a corresponding contour of a probe cover. The moving mechanism 65 further comprises a moving device 67, especially a compression spring, which is supported by a rim 20.1 of the movable portion 20. An axial force exerted on the probe cover or the head portion 14 in the proximal direction may lead to an axial displacement of the adapter 66 in the proximal direction, especially against a reaction force exerted by the moving device 67. As an alternative, the moving device 67 may be provided in the form of a motor-driven mechanism which can be positioned in predefined axial positions.

Figure 14:
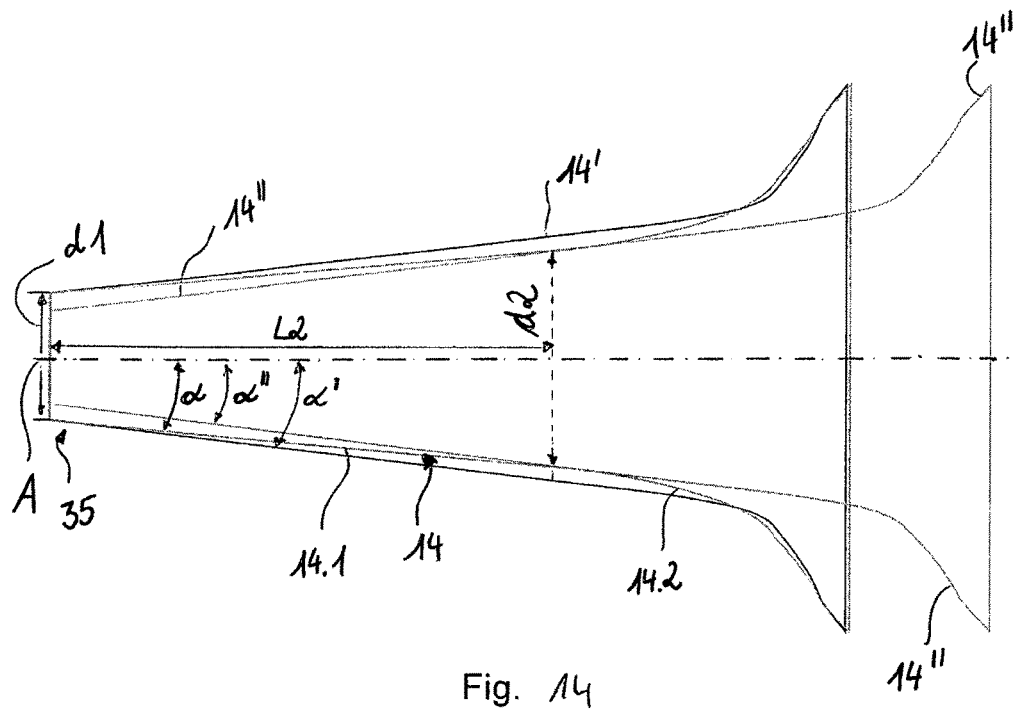
FIG. 14 schematically shows a side view of the head portion of an embodiment of an otoscope according to the present invention in comparison with two head portions of an otoscope of the prior art.

In FIG. 14, the shape of a head portion 14 according to one embodiment of the present invention is shown in comparison with the shape of a first head portion 14' according to prior art and a second head portion 14" according to prior art. Thereby, the shape of a probe cover (not shown) according to the present invention can geometrically correspond with this shape. In particular, the probe cover exhibits a shape or an inner contour which geometrically corresponds with the shape or outer contour of the head portion. In particular, the probe cover exhibits the same shape as the head portion, a wall thickness of the probe cover preferably being in the range of 0.02 mm to 0.05 mm. Therefore, an outer shape or contour of the probe cover can be characterized by the measurements stated with respect to the head portion, adding 0.04 to 0.1 mm in diameter.

It can be seen that the head portion 14 has a conical section 14.1 and a parabolic section 14.2. The conical section 14.1 can also be described as an insertion section which is provided for getting in contact with soft connective tissue. At a transition area between the conical section 14.1 and the parabolic section 14.2, the head portion 14 has a diameter d2. The conical section 14.1 is provided along a specific length L2.

As compared with the first head portion 14', which is preferably provided for children older than 12 month or for adults, the shape of the head portion 14 is more slender, and an opening angle α of the conus of the conical section 14.1 is smaller, i.e. more obtuse. As compared with the second head portion 14", which is preferably provided for infants younger than 12 month, a distal tip 35 of the head portion 14 exhibits a diameter d1 which is considerably larger. Also, the opening angle α of the head portion 14 is smaller, i.e. more obtuse. In other words: The opening angle α is more obtuse than the opening angle α' of the head portion 14' or than the opening angle α" of the head portion 14". The opening angle α is preferably in the range of 3° to 10°, further preferred 4° to 8°, especially 5° or 6°. Such a small opening angle can ensure that any friction between an inner lateral surface of the ear canal and the probe cover can be minimized, especially in a circumferential direction (due to relative rotation). The ratio d1:d2 of the inventive head portion 14 is bigger as compared with the conventional head portions 14' and 14".

The specific length L2 is preferably in the range of 18 mm to 22 mm, especially 20 mm. A diameter d1 of the distal tip 35 is preferably in the range of 4.7 mm to 5.2 mm, more preferably 4.8 mm to 5 mm, especially 4.9 mm. A diameter d2, especially at a distance of 20 mm from the distal tip 35, is preferably in the range of 8 mm to 9 mm, especially 8.5 mm.

Figure 15:
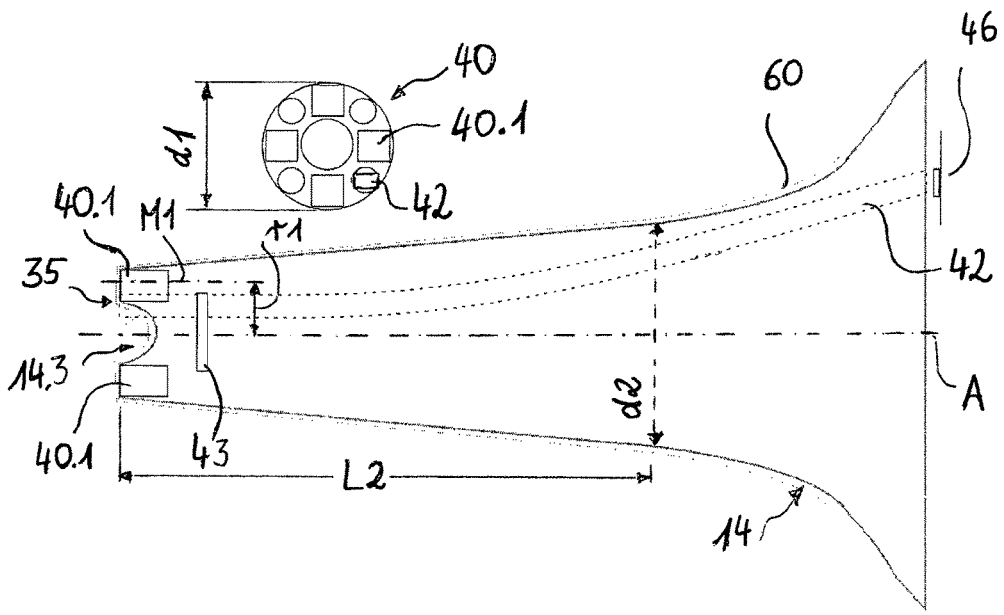
FIG. 15 schematically shows a cross-sectional side view of the head portion of an embodiment of an otoscope according to the present invention as well as a front view on the distal tip of the head portion.

FIG. 15 shows a head portion 14 including at least one light guide or light source 42 and an electronic imaging unit 40 comprising several eccentrically arranged, i.e. radially offset cameras 40.1. Light is guided from one or more light sources 46 via the light guide 42 to the distal tip 35. Along a specific length L2, the head portion 14 has a conical shape. The specific length L2 can be defined as the length along which the head portion 14 can be in contact with the patient's tissue, especially with soft connective tissue confining the outer ear canal, at least partially. The specific length L2 is preferably in the range of 18 mm to 22 mm, especially 20 mm. The diameter d1 of the distal tip 35 is preferably in the range of 4.7 mm to 5.2 mm, more preferably 4.8 mm to 5 mm, especially 4.9 mm. The diameter d2, especially at a distance of 20 mm from the distal tip 35, is preferably in the range of 8 mm to 9 mm, especially 8.5 mm. A probe cover 60 can be provided over the head portion 14. The total length of the head portion is in the range between 26 mm and 34 mm, preferably 28 mm and 32 mm, more preferable 29 mm and 31 mm, especially around 30.3 mm.

The cameras 40.1 are arranged in a radial distance r1 between the longitudinal axis A and a middle axis M1 of the respective camera 40.1. The (eccentric) distance r1, i.e. the radial offset is preferably in the range of 1 mm to 2.5 mm, more preferable in the range of 1.5 mm to 2 mm, especially about 1.7 mm, 1.8 mm or 1.9 mm. The ratio r1:d1 is preferably in the range of 0.35 to 0.55, especially 0.4, 0.45 or 0.5.

At a distal tip, the head portion 14 exhibits an indentation 14.3. The indentation 14.3 is arranged concentrically with respect to the longitudinal axis A. The indentation 14.3 can be provided with, e.g., a parabolic or cylindrical shape. The indentation 14.3 provides a cavity for accommodating parts of the probe cover 60, in particular a folded or compressed portion (reservoir) of the probe cover 60.

Figure 16:
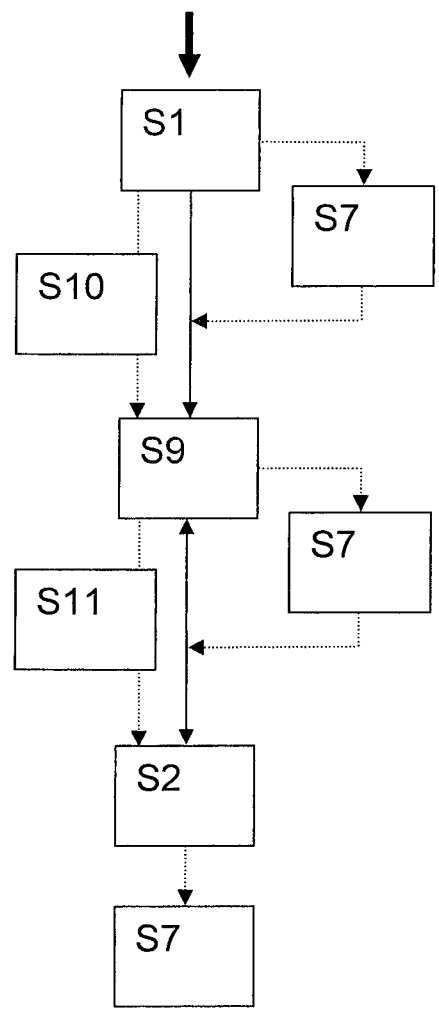
FIG. 16 schematically shows a diagram of steps of a method according to embodiments of the invention.

FIG. 16 shows a diagram of steps S1, S2, S7, S9, S10 and S11. Step S1 comprises introducing a head portion of an otoscope in conjunction with an at least partially transparent probe cover put over the head portion into an ear canal of a subject's outer ear, whereby an electronic imaging unit positioned at a distal end of the head portion is introduced. Step S2 comprises using the electronic imaging unit to capture at least one image from an observation point arranged on the at least one optical axis. Step S7 comprises displacing the electronic imaging unit and/or at least one light source. Step S9 comprises relatively moving at least a portion of the probe cover with respect to at least one optical axis of an optical electronic imaging unit accommodated within the head portion. Preferably, step S9 comprises axially moving a proximal portion of the probe cover and radially moving a distal portion of the probe cover. Step S10 comprises detecting a force exerted on the probe cover or the head portion. Step S11 comprises motion detection of the probe cover.

Step S9 may be adjusted in dependence on two different scenarios: relatively moving at least a portion of the probe cover can be carried out in dependence on further axial insertion of the head portion (i.e. during insertion of the head portion), or relatively moving at least a portion of the probe cover can be carried out only in case the head portion is arranged at an end position, i.e. the head portion is not introduced any further.

Relatively moving at least a portion of the probe cover in dependence on further axial insertion of the head portion may be favorable with respect to reduced friction between the probe cover and the inner lateral surface of the head portion. Thereby, preferably, the head portion is introduced further, but the relative position of the probe cover with respect to the inner lateral surface of the ear canal remains the same, at least approximately. In other words: friction only occurs between an inner surface of the probe cover and the head portion. Such a relative motion may be assisted by an axial force exerted on the head portion in a distal direction by the user/layperson.

Relatively moving at least a portion of the probe only in case the head portion is arranged at an end position may be favorable with respect to a minimum risk of any artifacts obstructing the view in the ear canal, especially as the distal tip of the head portion is not moved any further with respect to the inner lateral surface. Consequently, it is highly improbable that any further ear wax adheres on the distal tip of the probe cover.

Step S7 may be carried out subsequent to step S1 and/or S9 and/or S2. Step S10 may be carried out during step S1 and/or subsequent to step S1 and/or during step S9. Step S11 preferably is carried out prior to step S2.

The invention claimed is:

1. An otoscope comprising:
   a handle portion allowing a user to manipulate the otoscope during its application;
   a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
   an at least partially transparent probe cover adapted to be disposed over the head portion;
   an electronic imaging unit positioned at the distal end of the head portion; and
   a probe cover mover configured to move at least a portion of the at least partially transparent probe cover, the probe cover mover configured to move at least the portion of the probe cover towards the proximal end with respect to at least one optical axis of the electronic imaging unit.

2. The otoscope according to claim 1 wherein the mover is configured to move at least the portion of the probe cover in a direction which is at least approximately parallel to the longitudinal axis.

3. The otoscope according to claim 2, wherein the mover is configured to move the probe cover by exerting a pulling force on the probe cover.

4. The otoscope according to claim 1, wherein the mover is configured to unfold a reservoir of the probe cover by stretching a distal portion of the probe cover.

5. The otoscope according to claim 1 wherein the electronic imaging unit exhibits at least one optical axis which is positioned radially offset from the longitudinal axis, the mover being configured to move at least the portion of the probe cover with respect to the at least one radially offset optical axis.

6. The otoscope according to claim 1 wherein the mover is configured for automatically initiating relative displacement of the probe cover based on mechanical reaction forces exerted by the probe cover on the mover.

7. The otoscope according to claim 1 wherein the mover comprises an adapter which is arranged to axially position the probe cover in at least one specific axial position relative to the head portion, wherein the adapter includes a fixing element for connecting the probe cover to the adapter.

8. The otoscope according to claim 7 wherein the adapter is arranged to axially position the probe cover in a first position, in which the probe cover can be coupled to the otoscope, and in a second position, in which a reservoir of the probe cover is displaced relative to the distal end of the head portion.

9. The otoscope according to claim 7 wherein the fixing element is adapted for engaging an inner lateral surface section of the probe cover or for engaging the probe cover along a lateral surface completely in a circumferential direction, section by section or along the whole circumference.

10. The otoscope according to claim 1 wherein the mover comprises an adapter which is movably mounted, and a moving device cooperating with the adapter.

11. The otoscope according to claim 10 wherein the moving device is arranged to exert a reaction force on the adapter.

12. The otoscope according to claim 11, wherein the reaction force on the adapter is in a distal axial direction.

13. The otoscope according to claim 10 wherein the mover is arranged to define a threshold value for a force exerted on the mover, the mover being configured to move at least the portion of the probe cover only if the threshold value is exceeded.

14. The otoscope according to claim 13, wherein the threshold value is for an axial force exerted backwards in a proximal direction.

15. The otoscope according to claim 10 wherein the mover comprises a motion sensor which is connected to the imaging unit or to at least one light source or to a logic unit of the otoscope, the motion sensor being configured to detect a motion of the mover or of the probe cover relative to the head portion.

16. The otoscope according to claim 10, wherein the adapter is axially movably mounted and the moving device preferably defining a first position of the adapter.

17. The otoscope according to claim 1 wherein the mover comprises a force detector.

18. The otoscope according to claim 1, further comprising a motion mechanism configured to allow displacement of the electronic imaging unit or at least one optical axis of the electronic imaging unit relative to the handle portion.

19. The otoscope according to claim 18 wherein the head portion or the handle portion exhibits a form-fit shape which provides a coupling for fixing the probe cover to the otoscope such that the probe cover does not move during displacement of the electronic imaging unit or the at least one optical axis by the motion mechanism.

20. The otoscope according to claim 18, wherein the motion mechanism is configured to allow at least partial rotation of the electronic imaging unit or the at least one optical axis about an axis of rotation, and wherein the axis of rotation corresponds to the longitudinal axis of the head portion.

21. The otoscope according to claim 1, wherein the probe cover is adapted to be put over a head portion of the otoscope, wherein, at a distal end, the probe cover exhibits a reservoir which allows for modifying a shape of the probe cover, including at least a shape of a distal end of the probe cover, in order to move the probe cover with respect to the head portion.

22. The otoscope according to claim 21 wherein the reservoir is provided by a portion of the probe cover which is arranged centrally at a distal tip of the probe cover, or by a portion of the probe cover which annularly overlaps an outer section of a distal tip of the probe cover, or by a plurality of concentric circular bends provided at a distal tip of the probe cover.

23. The otoscope according to claim 21 wherein at a proximal end, the probe cover exhibits a protrusion which is arranged to axially position the probe cover with respect to the head portion.

24. The otoscope according to claim 21 wherein the probe cover is a double-ply probe cover, the reservoir being provided by an inner shell of the double-ply probe cover, wherein at least one gap or groove between shells of the probe cover provides a gas conduit.

25. The otoscope according to claim 24 wherein the probe cover exhibits two shells which both provide a form-fit protrusion, adapted for interlocking with the probe cover mover, wherein the protrusions lie on top of each other.

26. The otoscope according to claim 21 wherein at least a portion of the probe cover is a molded plastic, made by deep-drawing or thermoforming, wherein the material of the probe cover is polypropylene.

27. The otoscope according to claim 21 wherein in a distal direction, the probe cover exhibits a decreasing wall thickness at least by half, the wall thickness being in the range between 10 micrometers and 100 micrometers, or between 5 micrometers and 70 micrometers, or between 20 micrometers and 50 micrometers.

28. The otoscope according to claim 21 wherein the probe cover is adapted to be fixed to at least one portion of the head portion or the handle portion of the otoscope in such a way that the probe cover does not move relative to the handle portion during rotation of the electronic imaging unit or the at least one optical axis.

29. The probe cover according to claim 21 wherein at a proximal end, the probe cover exhibits a radially protruding discoid collar, which is arranged for fixing the probe cover at a stationary portion of the head portion or at the handle portion.

30. The otoscope according to claim 1, wherein the probe cover is adapted to be put over the head portion of the otoscope, wherein, at a distal end, the probe cover exhibits a reservoir which allows for modifying a shape of the probe cover including at least a shape of a distal end of the probe cover, in order to move the probe cover with respect to the handle portion, wherein at a proximal end, the probe cover exhibits a protrusion which is arranged for axially positioning the probe cover with respect to the head portion.

31. The otoscope according to claim 1, wherein the probe cover is adapted to be put over the head portion of the otoscope, wherein, at a distal end, the probe cover exhibits a reservoir which allows for modifying a shape of the probe cover including at least a shape of a distal end of the probe cover, in order to move the probe cover with respect to the handle portion, wherein the reservoir is provided by a portion of the probe cover which is arranged centrally at a distal tip of the probe cover, or by a portion of the probe cover which annularly overlaps an outer section of a distal tip of the probe cover, or by a plurality of concentric circular bends provided at a distal tip of the probe cover, and wherein the probe cover is a double-ply probe cover, the reservoir being provided by an inner shell of the double-ply probe cover, wherein at least one gap or groove between shells of the probe cover provides a gas conduit.

32. The otoscope according to claim 1, wherein the electronic imaging unit is positioned at a distal tip of the head portion.

33. An otoscope comprising:
 a handle portion allowing a user to manipulate the otoscope during its application;
 a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
 an at least partially transparent probe cover adapted to be disposed over the head portion;
 an electronic imaging unit positioned at the distal end of the head portion; and
 a probe cover mover configured to move at least a portion of the at least partially transparent probe, the probe cover mover configured to move at least the portion of the probe cover towards the proximal end with respect to at least one optical axis of the electronic imaging unit,
 wherein the mover comprises an adapter which is movably mounted, and a moving device cooperating with the adapter, wherein the moving device is arranged to exert a reaction force on the adapter, and wherein the mover is arranged to define a threshold value for a force exerted on the mover, the mover being configured to move at least the portion of the probe cover only if the threshold value is exceeded.

34. The otoscope according to claim 33, wherein the electronic imaging unit is positioned at a distal tip of the head portion.

35. The otoscope according to claim 33, wherein the adapter is axially movably mounted.

36. The otoscope according to claim 33, wherein the moving device defines a first position of the adapter.

37. The otoscope according to claim 33, wherein the reaction force on the adapter is in a distal axial direction.

38. The otoscope according to claim 33, wherein the threshold value is for an axial force exerted backwards in a proximal direction.

39. An otoscope comprising:
 a handle portion allowing a user to manipulate the otoscope during its application;

a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;

an at least partially transparent probe cover adapted to be disposed over the head portion;

an electronic imaging unit positioned at the distal end of the head portion; and a probe cover mover configured to move at least a portion of the at least partially transparent probe cover, the probe cover mover configured to move at least the portion of the probe cover with respect to at least one optical axis of the electronic imaging unit, wherein the mover is configured for automatically initiating relative displacement of the probe cover based on mechanical reaction forces exerted by the probe cover on the mover, wherein the mover comprises an adapter which is arranged to axially position the probe cover in at least one specific axial position relative to the head portion, and wherein the adapter is arranged to axially position the probe cover in a first position, in which the probe cover can be coupled to the otoscope, and in a second position, in which the reservoir of the probe cover is displaced relative to the distal end of the head portion.

40. The otoscope according to claim 39, wherein the electronic imaging unit is positioned at a distal tip of the head portion.

41. An otoscope comprising:
a handle portion allowing a user to manipulate the otoscope during its application;
a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
an at least partially transparent probe cover adapted to be disposed over the head portion;
an electronic imaging unit positioned at the distal end of the head portion;
a probe cover mover configured to move at least a portion of the at least partially transparent probe cover the probe cover mover configured to move at least the portion of the probe cover towards the proximal end with respect to at least one optical axis of the electronic imaging unit; and
a motion mechanism configured to allow displacement of the electronic imaging unit or at least one optical axis of the electronic imaging unit relative to the handle portion, wherein the head portion or the handle portion exhibits a form-fit shape which provides a coupling for fixing the probe cover to the otoscope such that the probe cover does not move during displacement of the electronic imaging unit or the at least one optical axis by the motion mechanism.

42. An otoscope comprising:
a handle portion allowing a user to manipulate the otoscope during its application;
a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
an at least partially transparent probe cover adapted to be disposed over the head portion, the probe cover being flexible;
an electronic imaging unit positioned at the distal end of the head portion; and
a probe cover mover configured to move at least a portion of the at least partially transparent probe cover, the probe cover mover configured to move the probe cover with respect to at least one optical axis of the electronic imaging unit.

43. A method of identifying objects in a subject's ear comprising the following steps:
providing an otoscope including:
a handle portion allowing a user to manipulate the otoscope during its application;
a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
an at least partially transparent probe cover adapted to be disposed over the head portion;
an electronic imaging unit positioned at the distal end of the head portion; and
a probe cover mover configured to move at least a portion of the at least partially transparent probe cover, the probe cover mover configured to move at least the portion of the probe cover towards the proximal end with respect to at least one optical axis of the electronic imaging unit;
introducing the head portion of the otoscope in conjunction with the at least partially transparent probe cover put over the head portion into an ear canal of a subject's outer ear, the head portion accommodating the electronic imaging unit which exhibits at least one optical axis;
moving at least a portion of the probe cover with respect to the at least one optical axis; and
using the electronic imaging unit to capture at least one image.

44. A method of providing electronic vision for identifying objects in a subject's ear, the method comprising the following steps:
providing an otoscope including:
a handle portion allowing a user to manipulate the otoscope during its application;
a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
an at least partially transparent probe cover adapted to be disposed over the head portion;
an electronic imaging unit positioned at the distal end of the head portion; and
a probe cover mover configured to move at least a portion of the at least partially transparent probe cover, the probe cover mover configured to move at least the portion of the probe cover towards the proximal end with respect to at least one optical axis of the electronic imaging unit;

introducing the head portion of the otoscope in conjunction with the at least partially transparent probe cover put over the head portion into an ear canal of a subject's outer ear, the head portion accommodating an optical electronic imaging unit which exhibits at least one optical axis;

detecting a force exerted on the head portion or the probe cover during introduction, including a force in a direction substantially parallel to a longitudinal axis of the head portion; and moving at least a portion of the probe cover with respect to the at least one optical axis.

45. A method of identifying and medically characterizing the eardrum in a subject's ear, the method comprising the following steps:

providing an otoscope including:
- a handle portion allowing a user to manipulate the otoscope during its application;
- a head portion exhibiting a substantially tapering form extending along a longitudinal axis of the head portion, wherein the head portion has a proximal end adjacent to the handle portion and a distal end, the distal end being smaller than the proximal end and adapted to be introduced in an ear canal of a patient's outer ear;
- an at least partially transparent probe cover adapted to be disposed over the head portion;
- an electronic imaging unit positioned at the distal end of the head portion; and
- a probe cover mover configured to move at least a portion of the at least partially transparent probe cover, the probe cover mover configured to move at least the portion of the probe cover towards the proximal end with respect to at least one optical axis of the electronic imaging unit;

introducing the head portion of the otoscope in conjunction with the at least partially transparent probe cover, which is put over the head portion, into an ear canal of a subject's outer ear, the head portion accommodating an optical electronic imaging unit which exhibits at least one optical axis;

detecting a force exerted on the head portion or the probe cover during introduction, including a force in a direction substantially parallel to a longitudinal axis of the head portion; and moving at least a portion of the probe cover with respect to the at least one optical axis, in dependence on a specific threshold value of a detected force;

using the electronic imaging unit to capture at least one image of the eardrum; and evaluating a medical condition of the eardrum by medically characterizing the eardrum based on at least one image captured of the eardrum.

* * * * *